United States Patent [19]

Wolter

[11] Patent Number: 5,756,767
[45] Date of Patent: May 26, 1998

[54] HYDROLYZABLE AND POLYHMERIZABLE SILANES

[76] Inventor: Herbert Wolter, Steinstrasse 21, D-97950 Gerchsheim-Grossrinderfeld, Germany

[21] Appl. No.: 856,939

[22] Filed: May 15, 1997

Related U.S. Application Data

[63] Continuation of Ser. No. 499,026, Jul. 6, 1995, abandoned.

[30] Foreign Application Priority Data

Jul. 6, 1994 [DE] Germany ............... 4423 811.8

[51] Int. Cl.$^6$ .............. C07D 305/00; C07D 309/00; C07D 321/00; C07D 323/00
[52] U.S. Cl. .............. 549/214; 549/215; 549/228; 549/229
[58] Field of Search ................. 549/214, 215, 549/228, 229

[56] References Cited

U.S. PATENT DOCUMENTS 3,932,464  1/1976  Kotzch et al. ............ 260/340.9
4,118,540  10/1978  Amort et al. ............ 428/447

FOREIGN PATENT DOCUMENTS 3407087  9/1985  Germany.
3536716  4/1987  Germany.
4125201  10/1992  Germany.

*Primary Examiner*—Mukund J. Shah
*Assistant Examiner*—Bruck Kifle
*Attorney, Agent, or Firm*—Michael J. Striker

[57] ABSTRACT

The hydrolyzable and polymerizable silanes have the formula I.

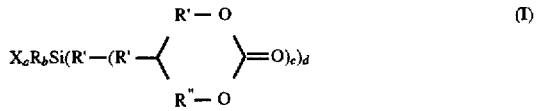

(I)

wherein

X is hydrogen, a halogen, a hydroxy, an alkoxy group, an acyloxy group, an alkylcarbonyl group, an alkoxycarbonyl group or —$NR^2_2$ group; wherein $R^2$ is hydrogen, an alkyl group or an aryl group;

R is an alkyl group, an alkenyl group, an aryl group, an alkylaryl group or an arylalkyl group;

R' is a substituted or unsubstituted alkylene group, arylene group, arylenealkylene group or alkylenearylene group, each having from zero to ten carbon atoms, wherein the substituted alkylene groups, the substituted arylene groups, the substituted arylenealkylene groups and the substituted alkylenearylene groups each have an oxygen atom, a sulfur atom and/or an amine group substituent; R" is a substituted or unsubstituted alkylene, arylene, alkylenearylene or arylenealkylene groups each having from 1 to 10 carbon atoms, wherein the substituted alkylene groups, the substituted arylene groups and the substituted alkylenearylene groups each have at least one oxygen atom, sulfur atom and/or amine group substituent;

wherein a=1, 2 or 3, b=0, 1 or 2 but a+b necessarily=1, 2 or 3; c=1, 2, 3, 4, 5 or 6 and d=4−a−b.

4 Claims, No Drawings

HYDROLYZABLE AND POLYHMERIZABLE SILANES

This is a file wrapper continuation of application, Ser. No. 08/499,026, filed on Jul. 6, 1995, now abandoned.

BACKGROUND OF THE INVENTION

The present invention relates to hydrolyzable and polymerizable silanes, methods of making them and methods of using them to make silicic acid polycondensates and/or -heteropolycondensates and polymerizates and/or heteropolymerizates.

Hydrolyzable, organically modified silanes have various applications in the manufacture of scratch-resistant coatings for different substrates, for making filling materials, adhesive and sealing materials or molded bodies. In those applications the silanes, either alone or in mixtures with each other or in the presence of additional hydrolyzable and/or condensable components, are hydrolytically condensed. The final hardening occurs thermally, photochemically, covalent-nucleophilically or is redox induced.

Thus scratch resistant coatings which are described, for example, in German Published Patent Application DE 3407087 C2 are formed by hydrolytic condensation of a mixture which, among other things, comprises, a hydrolyzable titanium or zirconium compound $MR_4$ and a hydrolyzable, organo-functional silane

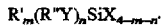

wherein R represents, e.g., halogen, hydroxy, alkoxy and acyloxy groups and R' represents, e.g., alkyl or alkenyl, R" represents, e.g., alkylene or alkenylene, and X represents a hydrolyzable group.

Adhesive and sealing materials are described in German Published Patent Application DE 3536716 A1 which could be obtained by hydrolytic condensation of one or more organosilanes of the general formula $R_mSiX_{4-m}$ and, as needed, one or more of the compounds of the formula $SiX_4$ and/or $R_n(R"Y)_pSiX_{4-n-p}$, wherein R and R" are independently, e.g., an alkyl group, alkenyl group, aryl group, alkylaryl group, an arylalkyl group, an alkenylaryl group or an arylalkenyl group; X, e.g., is hydrogen, halogen, a hydroxy group, an alkoxy group or an acyloxy group; and Y, e.g., represents a halogen or an unsubstituted or substituted amino, amide, aldehyde, alkylcarbonyl, carboxy, hydroxy, mercapto or cyano group.

Commercial silanes with reactive double bonds are known, such as (meth)acryloxysilanes of the following formula:

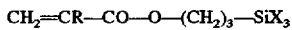

wherein R is hydrogen or methyl and X represents, e.g., a halogen or alkoxy group. These silanes are hydrolyzable and polymerizable and can be used for manufacture of the above-described systems. They offer the great advantage that the resultant coating, the resultant filling material, adhesive material, sealing material or the resultant molded body can be hardened by polymerization at the reactive double bond thermally and/or photochemically.

In all the above systems it is disadvantageous that a volume decrease occurs in the polymerization, i.e. a so-called hardening shrinkage occurs, which also leads to stresses and strains in the coating, or in the resultant filling material, adhesive material, sealing material or the resultant molded body, and/or to a loss of bulk adherence. These stresses and strains can lead to macroscopic break-up, i.e. to tears or to pieces breaking off, as for example to optical interference phenomenon (local changes in the index of refractions, interference sites), to reduced mechanical stability, to surface structures, etc. The loss of bulk adherence is particularly troublesome for formation of molded bodies (e.g. in injection molding) and in bulk molding (optical gratings, etc).

Hydrolyzable and polymerizable silanes, which have one or more spiro group and are hydrolytically condensable alone, or together with other hydrolyzable components, and are hardened by ring opening followed by polymerization, are described in German Published Patent Application DE 4125201 C1. These ring openings of course counteract shrinkage on hardening. Inspite of that, there is still a need for further development e.g. to improve biological degradability.

SUMMARY OF THE INVENTION

It is an object of the present invention to provide new organically modified silanes, which are hydrolyzable and polymerizable, which alone, in mixtures or together with other hydrolyzable, condensable or polymerizable components can be used to make scratch-resistant coatings, filling materials, adhesive materials or sealing materials, molded bodies and embedded materials.

It is another object of the present invention to provide new organically modified silanes of the above-described type for the above-described application which undergo a reduced volume decrease on hardening, which have a satisfactory substrate adherence and which have improved biological degradability.

It is an additional object of the present invention to provide new organically modified silanes of the above-described type which are universally usable in applications in which a reduced shrinkage on hardening is required and which can be built into an inorganic-organic compound system, i.e. into an inorganic-organic network.

These objects and others are attained according to the invention by the hydrolyzable and polymerizable silanes of the formula I,

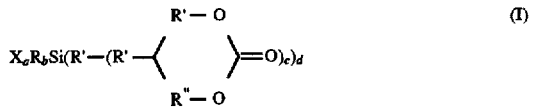

wherein
- X represents hydrogen, a halogen group, a hydroxy group, an alkoxy group, an acyloxy group, an alkylcarbonyl group, an alkoxycarbonyl group or a $-NR^2{}_2$; $R^2$ is hydrogen, an alkyl group or an aryl group;
- R represents an alkyl group, an alkenyl group, an aryl group, an alkylaryl group or an arylalkyl group;
- R' represents a member selected from the group consisting of substituted and unsubstituted alkylene groups, arylene groups, arylenealkylene groups and alkylenearylene groups each having from zero to ten carbon atoms, wherein the substituted alkylene groups, the substituted arylene groups, the substituted arylenealkylene groups and the substituted alkylenearylene groups each have at least one oxygen atom, sulfur atom and/or amine group substituent; R" is a member of the group consisting of substituted and unsubstituted alkylene, arylene, alkylenearylene and arylenealkylene groups each having from 1 to 10 carbon atoms, wherein the substituted alkylene groups, the substituted arylene groups and the substituted alkylenearylene groups each have at least one oxygen atom, sulfur atom and/or amine group substituent;

wherein a=1, 2 or 3 and b=0, 1 or 2, but necessarily a+b=1, 2 or 3; and c=1, 2, 3, 4, 5 or 6 and d=4−a−b.

The X groups are hydrolyzable and the units with the index c and/or d is polymerizable.

The alkyl groups above are, e.g., straight chain, branched or cyclic groups with from 1 to 20 carbon atoms, particularly with 1 to 10 carbon atoms, and advantageously are lower alkyl groups with from 1 to 6 carbon atoms. Particular examples of appropriate alkyl groups include methyl, ethyl, n-propyl, i-propyl, n-butyl, s-butyl, t-butyl, i-butyl, n-pentyl, n-hexyl, cyclohexyl, 2-ethylhexyl, dodecyl and octadecyl groups.

The alkenyl groups are, e.g., straight chain, branched or cyclic groups with from 2 to 20, advantageously from 2 to 10, carbon atoms and advantageously lower alkenyl groups with from 2 to 6 carbon atoms, such as vinyl, allyl and 2-butenyl.

Preferred aryl groups include phenyl, biphenyl and naphthyl groups. The alkoxy, acyloxy, alkylcarbonyl, alkoxycarbonyl and amine-containing groups advantageously derived from the above-described alkyl and aryl groups. Special examples are methoxy, ethoxy, n- and i-propoxy, n-, i-, s- and t-butoxy, methylamino, ethylamino, dimethylamino, diethylamino, N-ethylanilino, acetyloxy, propionyloxy, methylcarbonyl, ethylcarbonyl, methoxycarbonyl, ethoxycarbonyl, benzyl, 2-phenylethyl and tolyl groups.

The above-named groups can have one or more substituents as needed, e.g. halogen, alkyl, hydroxyalkyl, alkoxy, aryl, aryloxy, alkylcarbonyl, alkoxycarbonyl, furfuryl, tetrahydrofurfuryl, amino, alkylamino, dialkylamino, trialkylammonium, amido, hydroxy, formyl, carboxy, mercapto, cyano, nitro, epoxy, $SO_3H$ and $PO_4H_2$.

The alkylene, arylene, arylenalkylene or alkylenarylene groups are derived from the above-described alkyl, aryl, arylalkyl and alkylaryl groups.

Fluorine, chlorine and bromine are particularly preferred halogens. Chlorine is especially preferred.

The group with index c can advantageously be a substituted or unsubstituted cyclic carbonate, in which the ring advantageously has from 5 to 6 atoms. However the ring could have up to 20 or more atoms.

The R' group can be the same or different and represents substituted and unsubstituted alkylene, arylene, arylenealkylene or alkylarylene groups with from 0 to 10 carbon atoms. The substituted groups can containing one or more oxygen, sulfur or an amino group substitutents. The group R" represents an alkylene, arylene, arylenealkylene or alkylenearylene groups with from 1 to 10 carbon atoms, which can include oxygen, sulfur or amine group substituents.

Without limitation the units or groups with the index c in formula I can advantageously be:

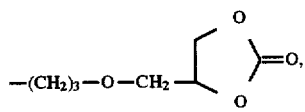

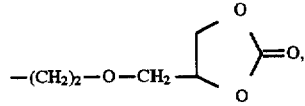

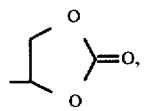

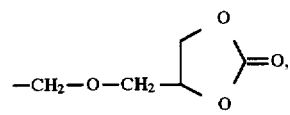

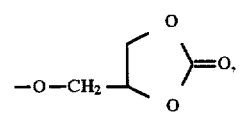

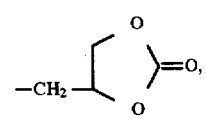

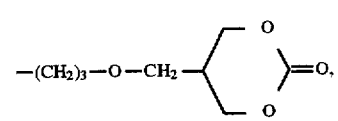

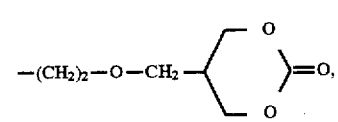

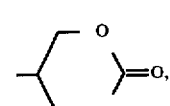

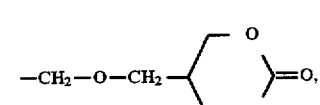

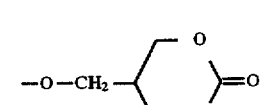

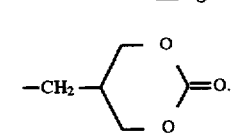

Without limitation additional examples of the units or groups with the index c in formula I can advantageously be:

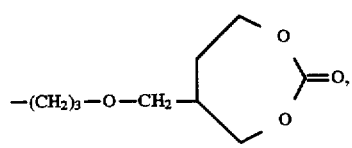

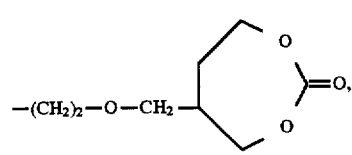

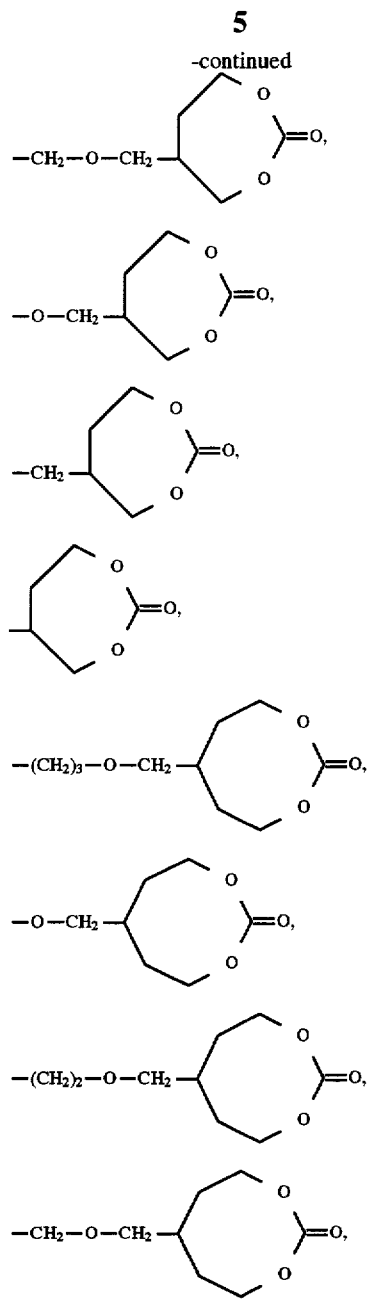
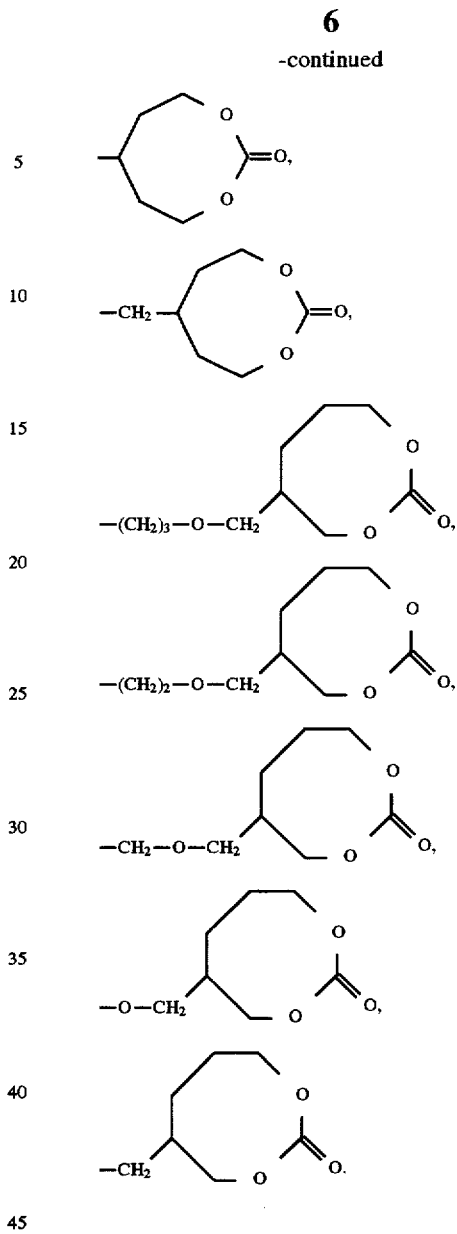
Without limitation particular examples of the silanes of formula I are as follows:
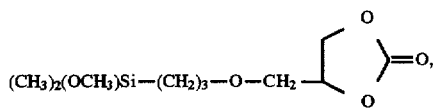
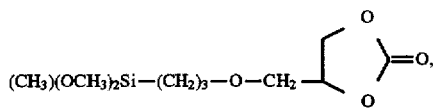
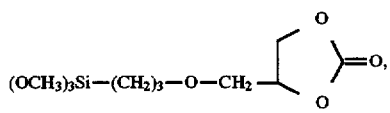

-continued
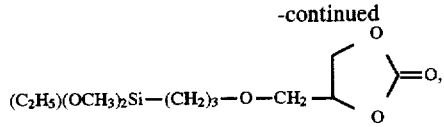
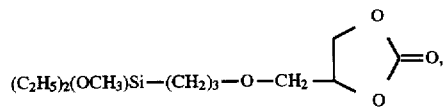
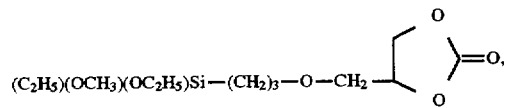
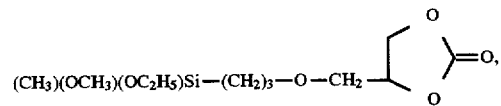
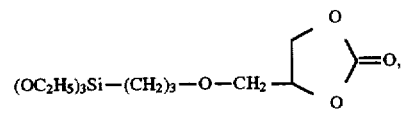
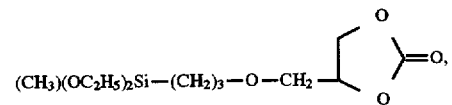
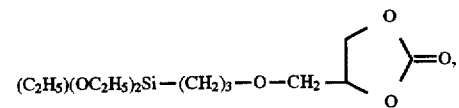
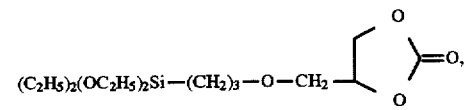
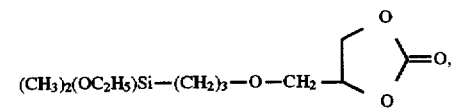
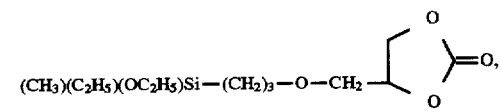
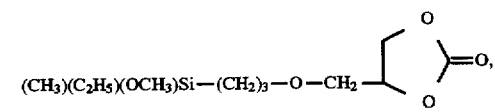
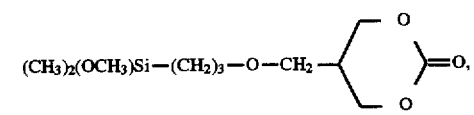
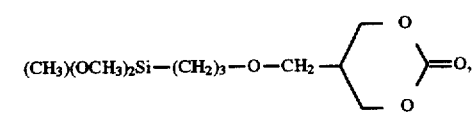
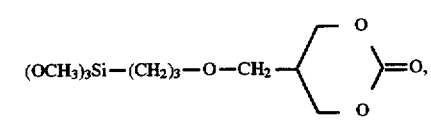

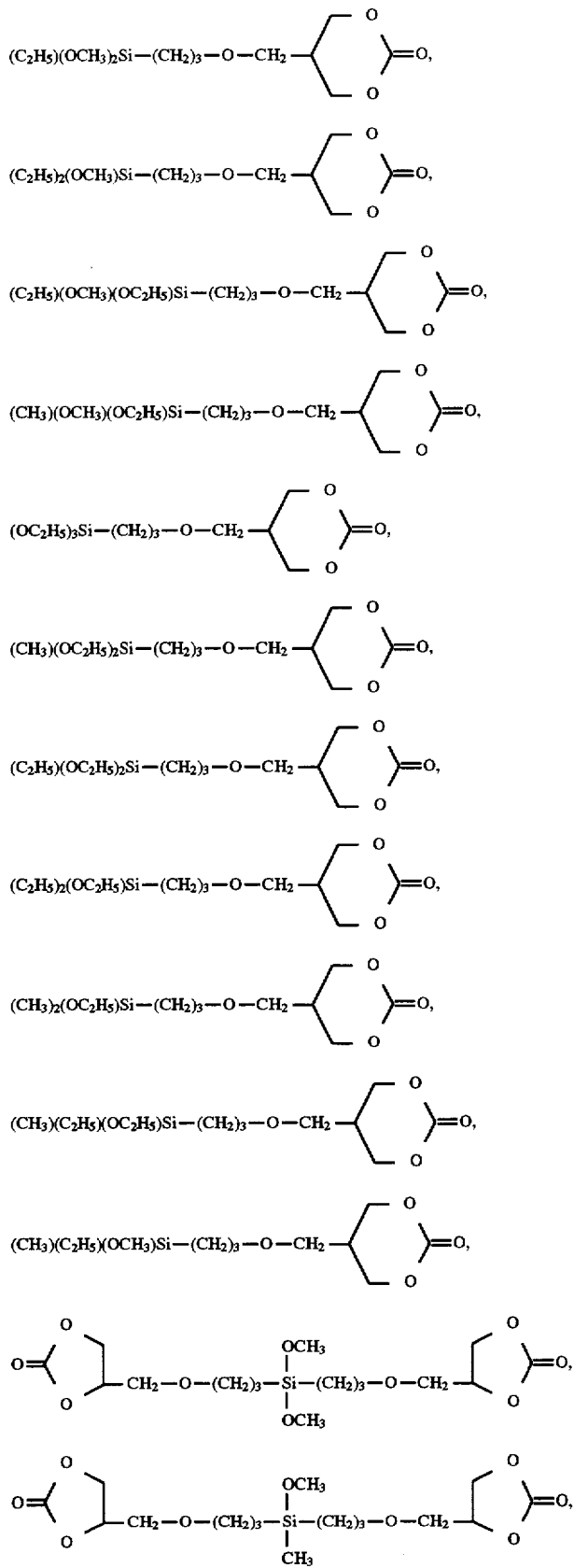

-continued
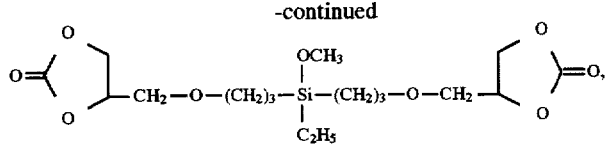
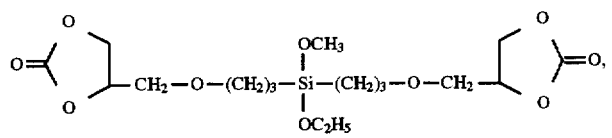
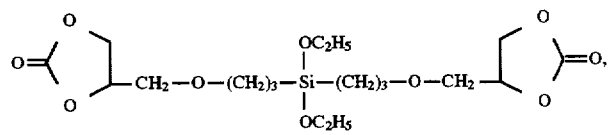
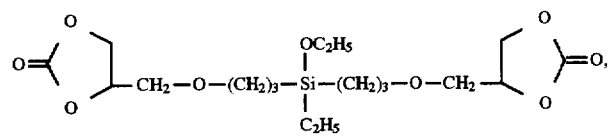
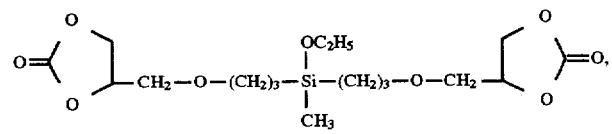
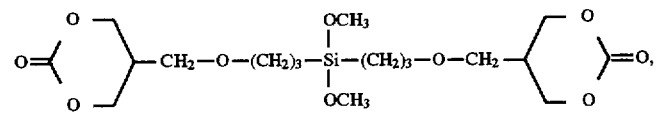
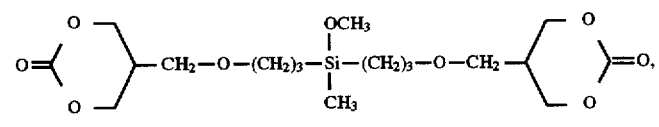
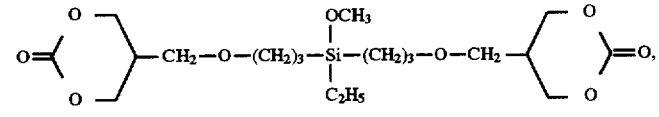
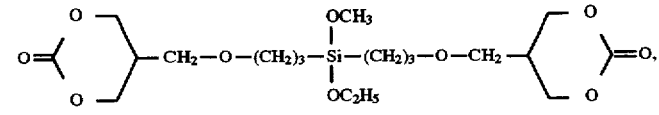
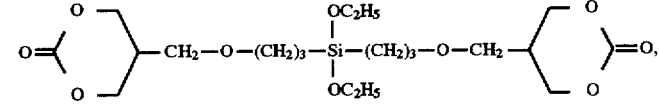
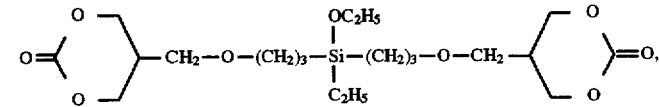
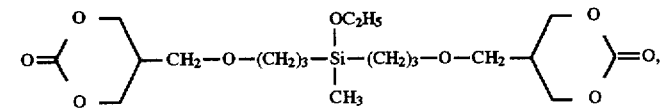

The silanes according to the invention can be made by a number of different methods.

Embodiment 1

In a first embodiment of the process for making the hydrolyzable and polymerizable silane of the formula I the process comprises carboxylating a silane reactant compound of the formula V,

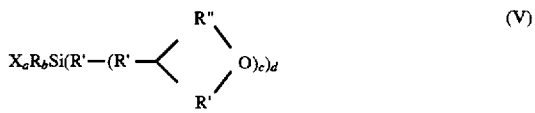
(V)

wherein a, b, c and d, X, R, $R^2$, R', R" are defined hereinabove in relation to the silane of formula I.

The general reaction scheme for this embodiment of the method is as follows:

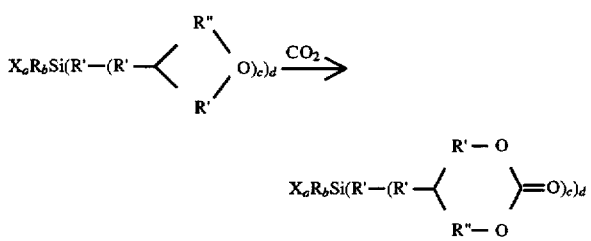

The preferred embodiment of this process uses the silane of the formula V' below and the product is a silane of the formula I'. The oxiran-ring of formula V' can be substituted.

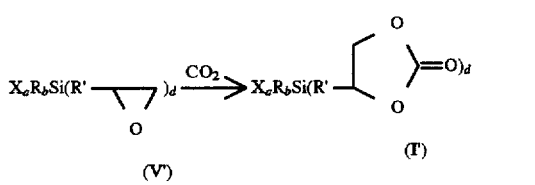

The following are concrete examples of the silane of formula V: glycidoxymethyltrimethoxysilane, glycidoxymethyltriethioxysilane, 2-glycidoxyethyltrimethoxysilane, 2-glycidoxyethyltriethoxysilane, 3-glycidoxypropyltrimethoxysilane, 3-glycidoxypropyltriethoxysilane, 3-glycidoxypropyltri (methoxyethoxy)silane, 3-glycidoxypropyltriacetoxysilane, 4-glycidoxybutyltrimethoxysilane, 4-glycidoxybutyltriethoxysilane, glycidoxy methyl(methyl) dimethoxysilane, glycidoxymetmethyl(ethyl) dimethoxysilane, glycidoxymethyl(phenyl) dimethoxysilane, glycidoxymethyl(vinyl)dimethoxysilane, glycidoxymethyl(dimethyl)methoxysilane, 2-glycidoxyethyl(methyl)dimethoxysilane, 2-glycidoxyethyl(ethyl)dimethoxysilane, 2-glycidoxyethyl (dimethyl)methoxysilane, 3-glycidoxypropyl(methyl) dimethoxysilane, 3-glycidoxypropyl(ethyl) dimethoxysilane, 3-glycidoxypropyl(dimethyl) methoxysilane, 4-glycidoxybutyl(methyl)dimethoxysilane, 4-glycidoxybutyl(ethyl)dimethoxysilane, 4-glycidoxybutyl (dimethyl)methoxysilane, bis-(glycidoxymethyl) dimethoxysilane, bis-(glycidoxymethyl)diethoxysilane, bis-(glycidoxyethyl)dimethoxysilane, bis-(glycidoxyethyl) diethoxysilane, bis-(glycidoxypropyl)dimethoxysilane, bis-(glycidoxypropyl)diethoxysilane, tris-(glycidoxymethyl) methoxysilane, tris-(glycidoxymethyl)ethoxysilane, tris-(glycidoxyethyl)methoxysilane, tris-(glycidoxyethyl) ethoxysilane, tris-(glycidoxypropyl)methoxysilane, tris-(glycidoxypropyl)ethoxysilane, glycidylmethyltrimethoxysilane, glycidylmethyltriethoxysilane, 2-glycidylethyltrimethoxysilane, 2-glycidylethyltriethoxysilane, 3-glycidylpropyltrimethoxysilane, 3-glycidylpropyltriethoxysilane, 3-glycidylpropyltri (methoxyethoxy)silane, 3-glycidylpropyltriacetoxysilane, 3,4-epoxycyclohexylmethyltrimethoxysilane, 3,4-epoxycyclohexylmethyltriethoxysilane, 3,4-epoxycyclohexylethytrimethoxysilane, 3,4-epoxycyclohexylpropyltrimethoxysilane and 3,4-epoxycyclohexylbutyltrimethoxysilane.

Silanes of the formula V' are commercially obtainable, e.g. in the case of the ABCR GmbH & Co. KG(Karlsruhe) the 3-glycidoxypropyldimethylethoxysilane, the (3-glycidoxypropyl)methyldiethoxysilane, the 3-glycoxypropylmethyl-di-isopropenoxysilane, the (3-glyoxypropyl)trimethoxysilane, the 2-(3,4-epoxycyclohexyl)ethyltrimethoxysilane or the [2-(3,4-epoxy-4-methylcyclohexyl)propyl]methyldiethoxysilane.

The first embodiment of the process is exemplified by the reaction of (3-glycidoxypropyl)trimethoxysilane with carbon dioxide:

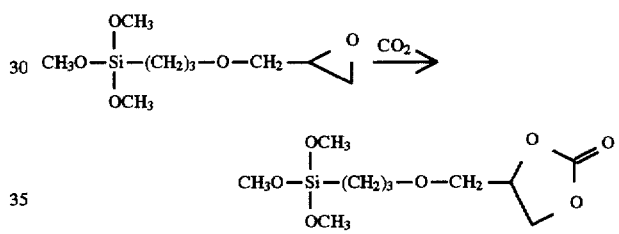

Embodiment 2

In a second embodiment of the process for making the hydrolyzable and polymerizable silane of the formula I the process comprises reacting a substituted or unsubstituted silane reactant compound of the formula VI,

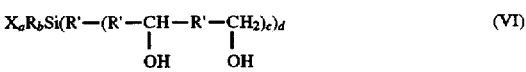
(VI)

with a carbonate of the formula R"—O—CO—O—R", wherein a, b, c and d, X, R, $R^2$, R', R" are defined hereinabove in relation to the silane of formula I. In this second embodiment of the process the reaction mechanism is as follows:

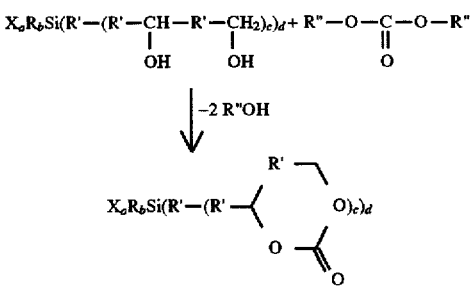

In a preferred embodiment of this second process a substituted or unsubstituted silane of formula VI' is used,

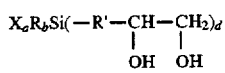 (VI')
in which the groups and indexes are the same or different and have the same significance as in formula I. The general reaction mechanism is:
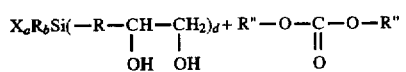
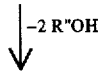
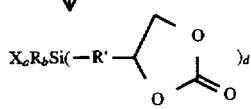
Without limitation specific examples of the salines of formula VI are as follows:
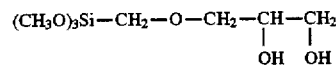
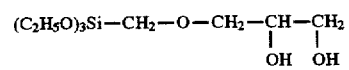
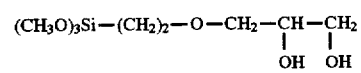
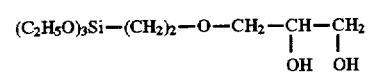
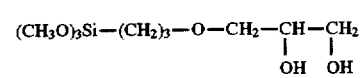
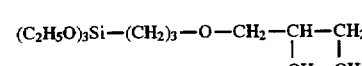
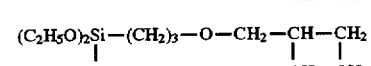
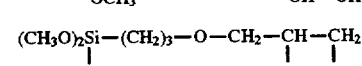
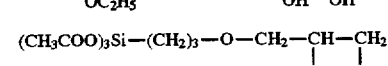
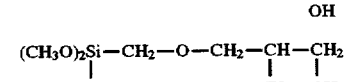
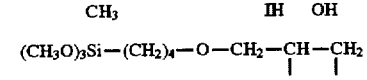
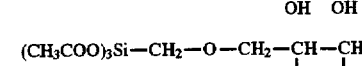
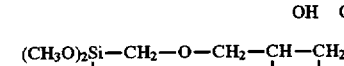
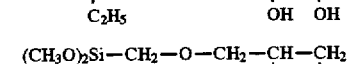
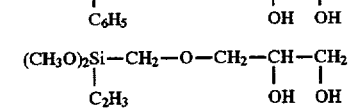
-continued
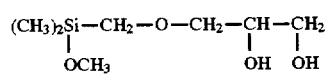
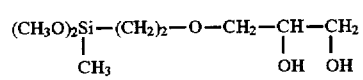
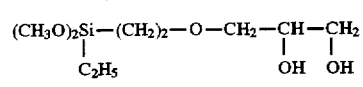
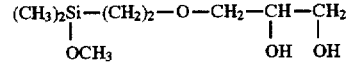
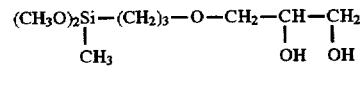
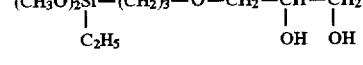
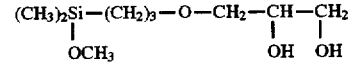
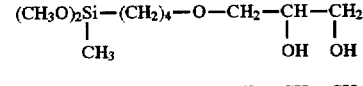
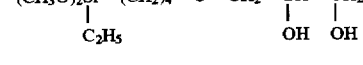
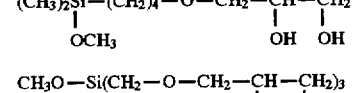
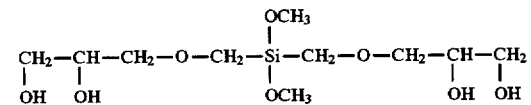
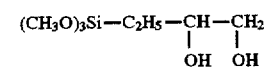
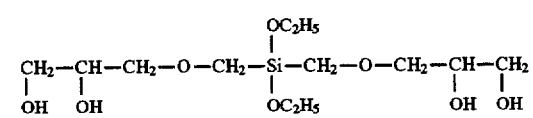
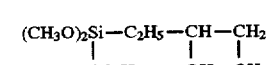
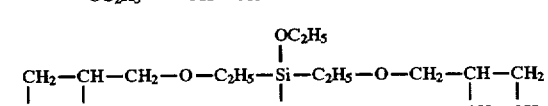
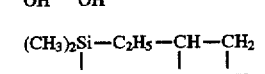
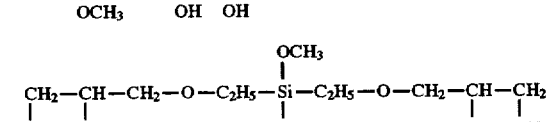
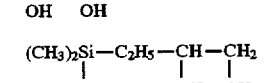

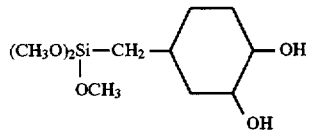
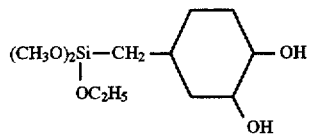
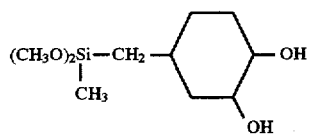
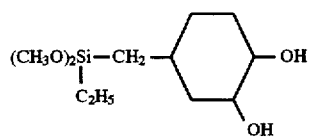
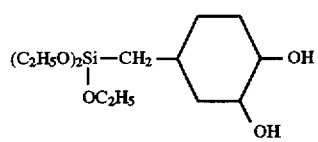
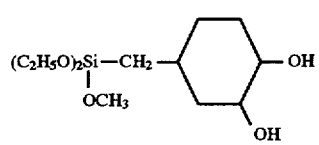
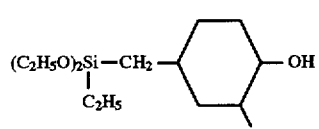
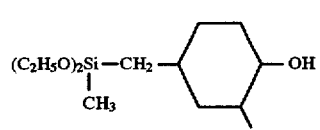
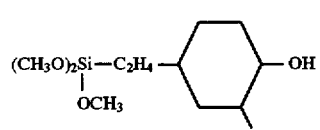
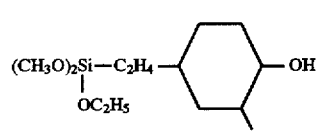
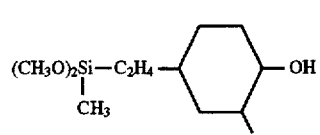
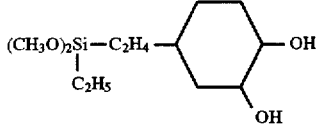
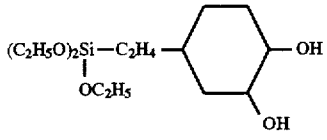
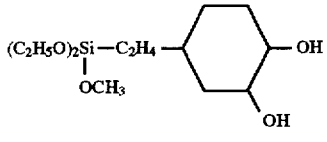
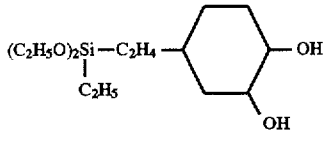
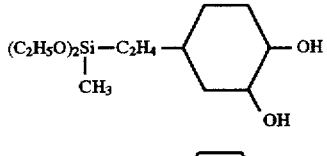
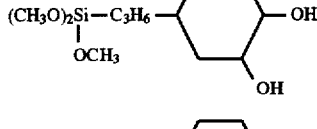
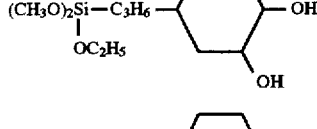
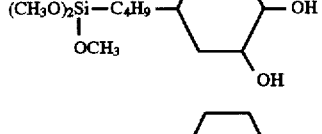
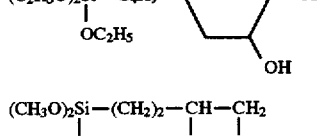
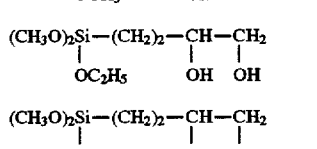
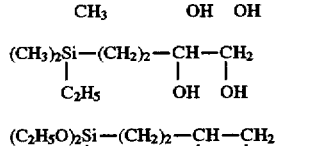

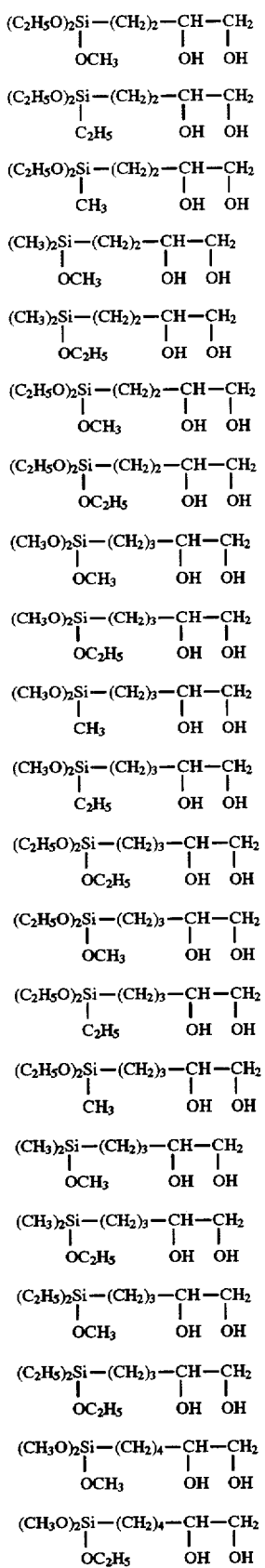

-continued

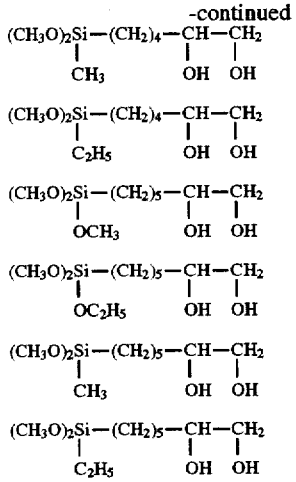

Embodiment 3

In a third embodiment a process for making the hydrolyzable and polymerizable silane of the formula I comprises the steps of carboxylating a reactant compound of formula VII.

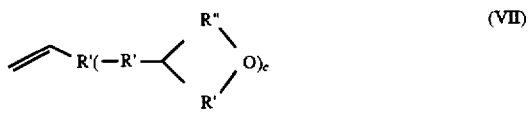  (VII)

to form an intermediate reaction product, and adding a silane compound of the formula $X_aR_bSiH_d$ or silane compound of the formula $X_aR_bSi(R'—SH)_d$ to the intermediate reaction product via the terminal C=C double bond, wherein the a, b, c and d, X, R, $R^2$, R', R" are as defined above in relation to formula I. The general reaction mechanism is:

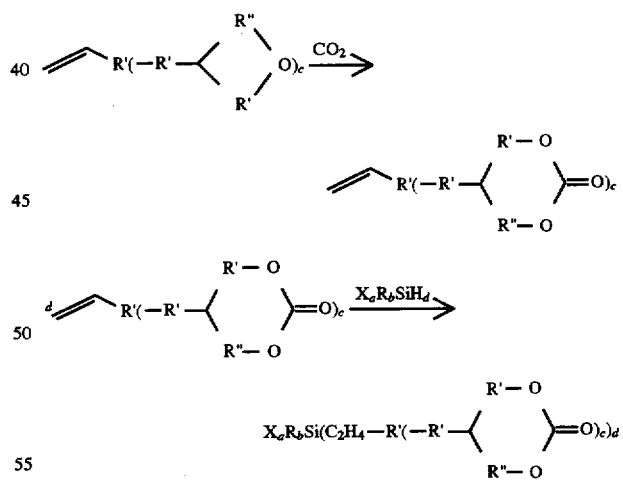

In a preferred example of the third embodiment of the process according to the invention the silane reactant compounds of formula VII are substituted or unsubstituted oxiranes of the formula VII' or of the formula VII", in which R' has the same significance as described above.

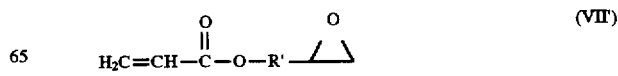  (VII')

-continued

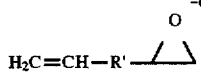 (VII")

The oxiran ring and/or the C=C double bond can be substituted. The reaction mechanism is as follows:

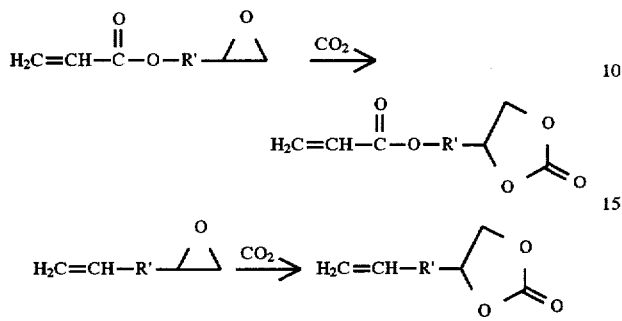

Specific examples of the oxiranes of formula VII are as follows:

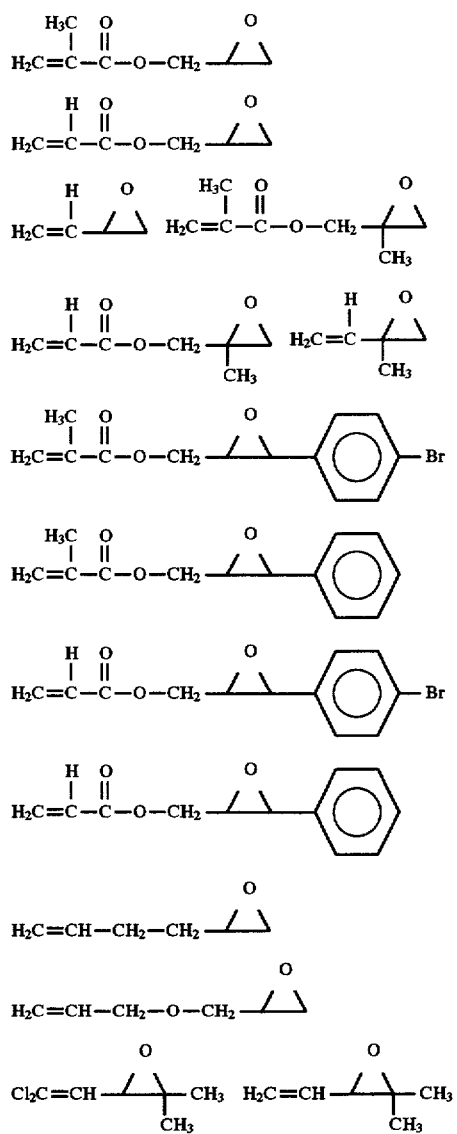

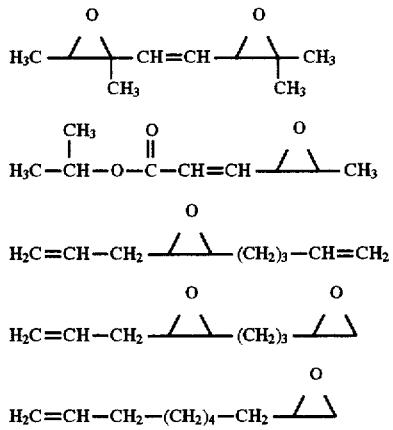

Concrete examples for the silane compounds of formula $X_aR_bSiH_d$ or silane compound of the formula $X_aR_bSi(R'—SH)_d$ are: $(CH_3O)_3SiH$, $(C_2H_5O)_3SiH$, $(CH_3O)_2(C_2H_5O)SiH$, $(CH_3O)(C_2H_5O)SiH$, $(CH_3)(CH_3O)_2SiH$, $(CH_3)_2(CH_3O)SiH$, $(CH_3)(C_2H_5O)_2SiH$, $Cl_2CH_3SiH$, $(CH_3)_2(C_2H_5O)SiH$, $(C_2H_5)(CH_3O)_2SiH$, $(C_2H_5)_2(CH_3O)SiH$, $(C_2H_5)(C_2H_5O)_2SiH$, $(C_2H_5)_2(C_2H_5O)SiH$, $(CH_3O)_2SiH_2$, $(C_2H_5O)_2SiH_2$, $(CH_3O)(C_2H_5O)SiH_2$, $(CH_3)(CH_3O)SiH_2$, $(CH_3)(C_2H_5O)SiH_2$, $ClCH_3SiH_2$, $(C_2H_5)(CH_3O)SiH_2$, $(C_2H_5)(C_2H_5O)SiH_2$, $ClC_2H_5SiH_2$, $(CH_3O)_3SiC_3H_6SH$, $(C_2H_5O)_3SiC_3H_6SH$, $(CH_3O)_2Si(C_3H_6SH)_2$, $(C_2H_5O)_2Si(C_3H_6SH)_2$, $(CH_3O)_2(C_2H_5O)SiC_3H_6SH$, $(CH_3O)(C_2H_5O)_2SiC_3H_6SH$, $(CH_3)(CH_3O)_2SiC_3H_6SH$, $(CH_3)(C_2H_5O)_2SiC_3H_6SH$, $(CH_3)Si(C_3H_6SH)_2$, $(CH_3)(C_2H_5O)Si(C_3H_6SH)_2$, $(CH_3)(CH_3O)(C_2H_5O)SiC_3H_6SH$, $(CH_3O)_3SiCH_2SH$, $(C_2H_5O)_3SiCH_2SH$, $(CH_3O)_2Si(CH_2SH)_2$, $(C_2H_5O)_2Si(CH_2SH)_2$, $(CH_3O)_2(C_2H_5O)SiCH_2SH$, $(CH_3O)(C_2H_5O)_2SiCH_2SH$, $(CH_3)(CH_3)_2SiCH_2SH$, $(C_3)(C_2H_5O)_2SiCH_2SH$, $(CH_3)(CH_3O)Si(CH_2SH)_2$, $(CH_3)(C_2H_5O)Si(CH_2SH)_2$, $(CH_3)(CH_3O)(C_2H_5O)SiCH_3SH$.

Embodiment 4

In a fourth embodiment a process for making the hydrolyzable and polymerizable silane of the formula I comprises the steps of carboxylating a substituted or unsubstituted alcohol compound of formula VIII,

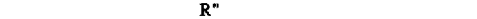 (VIII)

to form an intermediate reaction product, and adding a silane compound of the formula $X_aR_bSiH_d$ or silane compound of the formula $X_aR_bSi(R'—NCO)_d$ to the intermediate reaction product, wherein the a, b, c and d, X, R, $R^2$, R', R" are as defined in relation to formula I above. The general reaction mechanism is:

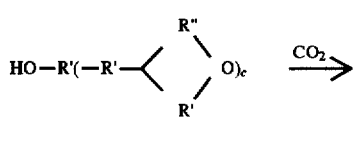

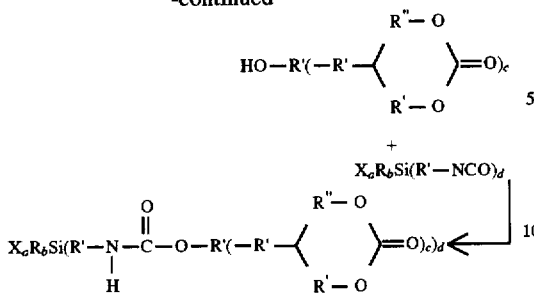

The preferred example of the alcohol of the formula VIII used in this method is, without limitation of the more general form of the fourth embodiment, an alcohol of the formula VIII in which the group R' has the same significance as above in formula I:

The general reaction mechanism is as follows:

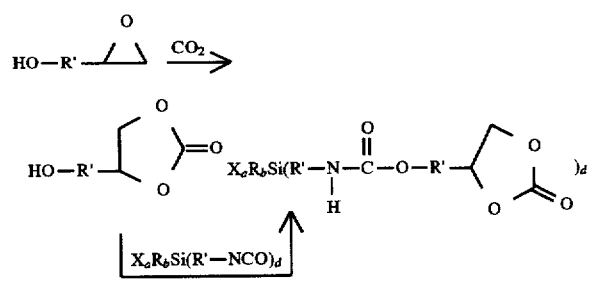

Specific examples of the reactant alcohol of formula VIII are:

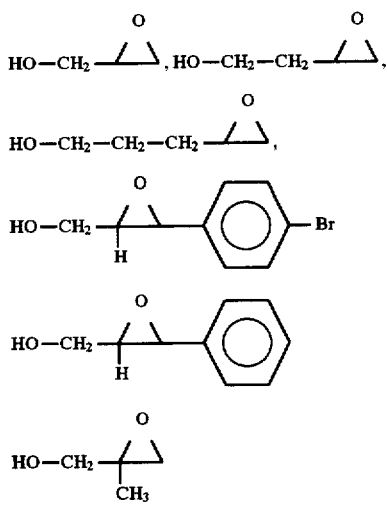

It is also possible to modify further the silanes according to the invention which are obtained by the above described methods and to provide them with other substituents.

The carbonate-silanes according to the invention are stable compounds and can be processed, either alone, or together with other hydrolyzable condensable and/or polymerizable components to form silicic acid polycondensates or silicic acid heteropolycondensates, whose final hardening occurs then by polymerization via ring opening of the cyclic carbonate-groups. The silanes according to the invention can be worked up also alone, or together with other hydrolyzable, condensable and/or polymerizable components, to form a polymerizate, which can be hardened by subsequent hydrolytic condensation.

Silicic acid(hetero)polycondensates, which are modified with organic groups, and methods for their manufacture (e.g. based on a hydrolytic condensation according to a Sol-Gel process) are known in great numbers. Condensates of this type are used in many different applications for a variety of purposes, e.g. as molded bodies, as lacquers for coatings, etc. Because of the many applications for this class of substances there is a continuous need for modification of the already known condensates to open new fields of use and to provide a further optimization of properties for certain applications.

The carbonate-silanes according to the invention are hydrolyzable and condensable in basic or acidic media, but so that the cyclic carbonate group is not opened prematurely. Because of that it is possible to build the carbonate-silanes according to the invention into an inorganic-organic network by hydrolytic condensation. The carbonate-silanes according to the invention contain hydrolyzable groups X, e.g. alkoxy groups, so that an inorganic network (Si—O—Si unit) can be built up because of them, while the carbonate groups contained in the molecular units with the index c and/or d (see formula I) can be polymerized into an organic network. Because of that it is possible to replace organically modified, hydrolyzable and condensable silanes in coatings, filling materials, adhesive materials and sealing materials, in molded bodies and imbedded bodies, in bulk material, in composites, castings, adhesives and bonding agents by the carbonate-silanes according to the invention.

The silanes according to the invention, are hydrolyzed and polycondensed, advantageously with other co-condensable components to build up the inorganic network. The polycondensation advantageously occurs according to a Sol-Gel process, such as, e.g., German Published Patent Applications DE-A1 2758414, 2758415, 3011761, 3826715 and 3835968.

The carbonate-silanes according to the invention, are ionically or covalently nucleophilically polymerized, advantageously with other co-condensable components to build up the organic network. The polycondensation advantageously can occur, e.g. thermally or photochemically, using methods which are described in German Published Patent Applications DE-A1 3143820, 3826715 and 3835968. The polymerization can be induced chemically, e.g. in two-component materials.

Polycarbonates of the following type

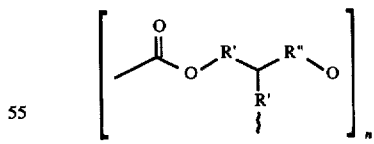

arise during the polymerization of the carbonate-silanes according to the invention. Further details regarding the ring-opening polymerization of cyclic carbonates is pointed out in the following literature:

Adv. Mater., 1994, 6, No. 1, 27–30 (1994).
Makromol. Chem. 193, 1207–1217 (1992).
Makromol. Chem. 186, 331–337 (1985).
Makromol. Chem., Macromol.Symp. 60, 119–131 (1992).

Aliphatic polycarbonates and copolymers containing aliphatic polycarbonates have already found wide applicability as biologically degradable materials. Aliphatic carbonate-silanes are thus important starting materials useful for manufacture of biologically degradable materials.

Compounds can be added as additional polymerizable components, which are radically and/or ionically and/or covalently-nucleophilically polymerizable. Radically polymerizable compounds, which can be added, are, e.g., those with C=C double bonds, such as, e.g. acrylate or methacrylate, whereby the polymerization occurs via the C=C double bonds. Ionically polymerizable compounds, which can be added, containing, e.g. ring systems, which are polymerizable cationically on ring opening, such as perhaps spiroorthoester, spiroorthocarbonate, bicyclic spiroorthoester, mono- or oligoepoxide, or ionically polymerizable on ring opening, such a cyclic carbonates. Compounds can also be added, which e.g. are both cationically and also radically polymerizable, such as methacryloyl-spiroorthoester. These polymerize radically via the C=C double bond and cationically with ring opening. The manufacture of these systems is, e.g., described in Journal f. prakt. Chemie, Volume 330, Part 2, 1988, pp. 316–318.

Further it is possible to add other known silane-bound cyclic systems, which can be copolymerized with the silanes according to the invention. Such systems are, for example, the spirosilanes as described in German Published Patent Application 4125201 C1 and the silanes which contain epoxides and, among other things, are used for manufacture of the carbonate-silanes according to the invention. Such systems have been already described in the methods of making the carbonate-silanes according to the invention.

The carbonate-silanes according to the invention provide highly reactive systems, which lead to poly(hetero) condensates, which, e.g., provide mechanically stable coatings, molded bodies and/or filling bodies when irradiated with UV radiation, heat treated or chemically induced after the shortest time. The carbonate-silanes according to the invention can be made by simple addition reactions and have a large number of reactive groups of different functionality when the reactant materials are properly selected.

The formation of a three-dimensional organic network is possible when two or more groups with the index c and/or d are present. The mechanical properties (e.g. flexibility) and the physico-chemical properties (adsorption, index or refraction, adherence, etc) of the poly(hetero)condensate are influenced by the spacing between the silicon atom and the carbonate group, i.e. by the chain length of the R' group, and by the presence of additional functional groups in this chain. Silicon- or glass-like properties of the poly(hetero) condensate are adjusted according to the type and number of the hydrolyzable groups (e.g. alkoxy groups) by the formation of an inorganic network.

When one considers the various possibilities of the cocondensable and copolymerizable components it is apparent that the silicic acid poly(hetero)condensates made from the carbonate-silanes according to the invention can be adjusted to and are useful in many ways in certain applications. Thus in all fields in which silicic acid(hetero)polycondensates are already used and also in new fields, e.g. the filed of optics, electronics, medicine, electro-optics, packaging materials for food, etc, these new silicic acid poly(hetero)condensates according to the invention are useful.

The carbonate-silanes according to the invention can be either used "as is" or in compositions, which contain additional ingredients according to the particular application, e.g. conventional lacquer ingredients, solvents, filling materials, photoinitiators, thermal and/or chemical initiators, thinning agents and pigments. The carbonate-silanes according to the invention or the compositions containing them are suitable, e.g. for making coatings, filling materials or bulk materials, for binders and injection molded bodies, for fibers, foils, adhesives, molded bodies and embedded materials. If aliphatic carbonate-silanes are used for these purposes, the materials obtained are also biologically degradable.

Because of the cyclic carbonate groups the carbonate-silanes according to the invention experience only a reduced shrinkage on hardening. If no shrinkage or even an expansion is desired, e.g. spirosilanes according to formula III can be added to the carbonate-silanes according to the invention. These silanes are described further hereinbelow. The shrinkage behavior also can be adjusted to the predetermined specifications of the particular application. Coatings and molded bodies made from the carbonate-silanes according to the invention have the advantage that they can be structured photochemically. Special fields of application include, e.g., metal, plastic, paper, ceramic coatings of substrates made by dipping, pouring, painting, spraying, electrostatic spraying, electroimmersion lacquering etc. They can also be useful for optical, electro-optical or electronic components, for making filling materials, for making scratch-resistant coatings, for making molded bodies, e.g. by injection molding, by casting or extrusion, and for making composites, e.g. fibers, filling materials or textiles.

Besides the carbonate-silanes according to the invention of formula I additional hydrolytically condensable compounds of silicon, boron, aluminum, phosphorus, zinc, lead, transition metals, lanthanides or actinides can be used. These compounds can be used either as such or in already precondensed form for making polycondensates. It is advantageous when at least 10 Mol %, particularly at least 80 Mol % and especially at least 90 Mol %, based on monomer content, of the reactant compounds used to make the silicic acid(hetero) polycondensates are silicon-compounds.

Likewise it is advantageous when the silicic acid(hetero) polycondensates comprise at least 5 Mol %, e.g. 25 to 100 Mol-%, particularly 50 to 100 Mol-% and especially 75 to 100 Mol-%, on the basis of monomer co n tent, of the carbonate-silane compounds.

Among the various additional hydrolytically condensable silicon-containing compounds which can be used tog ether with the silanes of formula I are the silicon-containing compounds of formula II,

$$R_a(R''Z')_b SiX_{4-(a'+b')} \qquad (II)$$

in an uncondensed or precondensed form, wherein the R, R", X and Z' groups can be the same or different and R" is selected from the group consisting of substituted and unsubstituted alkylene and substituted and unsubstituted alkenylene groups, the substituted alkylene and substituted alkenylene groups each having at least one substituent selected from the group consisting of oxygen atom, sulfur atom and —NH group; Z' is selected from the group consisting of halogen and substituted and unsubstituted amine, amide, aldehyde, alkylcarbonyl, carboxy, mercapto, cyano, alkoxy, alkoxycarbonyl, sulfonic acid, phosphoric acid, acryloxy, methacryloxy, epoxy and vinyl groups; and a'=0, 1, 2 or 3 and b'=0, 1, 2 or 3, with a'+b' necessarily=1, 2 or 3; and R and X are as defined hereinabove in connection with the silanes of formula I.

The silanes of formula II are described, e.g., in German Patent Application DE 34 07 087 C2.

The alkyl groups above are, e.g., straight chain, branched or cyclic groups with from 1 to 20 carbon atoms, particularly with 1 to 10 carbon atoms, and advantageously are lower alkyl groups with from 1 to 6 carbon atoms. Particular examples of appropriate alkyl groups include methyl, ethyl, n-propyl, i-propyl, n-butyl, s-butyl, t-butyl, i-butyl, n-pentyl, n-hexyl, cyclohexyl, 2-ethylhexyl, dodecyl and octadecyl groups.

The alkenyl groups are, e.g., straight chain, branched or cyclic groups with from 2 to 20, advantageously from 2 to 10, carbon atoms and advantageously lower alkenyl groups with from 2 to 6 carbon atoms, such as vinyl, allyl and 2-butenyl.

Preferred aryl groups include phenyl, biphenyl and naphthyl groups.

The alkoxy, acyloxy, alkylcarbonyl, alkoxycarbonyl and amine-containing groups advantageously derived from the above-described alkyl and aryl groups. Special examples are methoxy, ethoxy, n- and i-propoxy, n- , i- , s- and t-butoxy, methylamino, ethylamino, dimethylamino, diethylamino, N-ethylanilino, acetyloxy, propionyloxy, methylcarbonyl, ethylcarbonyl, methoxycarbonyl, ethoxycarbonyl, benzyl, 2-phenylethyl and tolyl groups.

The above-named groups can have one or more substituents as needed, e.g. halogen, alkyl, hydroxyalkyl, alkoxy, aryl, aryloxy, alkylcarbonyl, alkoxycarbonyl, furfuryl, tetrahydrofurfuryl, amino, alkylamino, dialkylamino, trialkylammonium, amido, hydroxy, formyl, carboxy, mercapto, cyano, nitro, epoxy, $SO_3H$ and $PO_4H_2$.

The alkylene, arylene, arylenalkylene or alkylenarylene groups are derived from the above-described alkyl, aryl, arylalkyl and alkylaryl groups.

Fluorine, chlorine and bromine are particularly preferred halogens.

Special examples of the hydrolytically condensable silicon-containing compounds of formula II are listed below.
$CH_3$—Si—$Cl_3$, $CH_3$—Si—$(OC_2H_5)_3$, $C_2H_5$—Si—$Cl_3$, $C_2H_5$—Si—$(OC_2H_5)_3$, $CH_2$=CH—Si—$(OC_2H_5)_3$, $CH_2$=CH—Si—$(OC_2H_4OCH_3)_3$, $(CH_3)_2$—Si—$Cl_2$, $CH_2$=CH—Si—$(OOCCH_3)_3$, $(CH_3)_2$—Si—$(OC_2H_5)_2$, $(C_2H_5)_3$—Si—Cl, $(C_2H_5)_2$—Si—$(OC_2H_5)_2$, $(CH_3)_2(CH_2$=CH)—Si—$Cl_2$, $(CH_3)_3$—Si—Cl, (t—$C_4H_9$)$(CH_3)_2$—Si—Cl, $(CH_3O)_3$—Si—$C_3H_6$—NH—$C_2H_4$—NH—$C_2H_4$—$NH_2$, $(CH_3O)_3$—Si—$C_3H_6$—SH, $(CH_3O)_3$—Si—$C_3H_6$—NH—$C_2H_4$—$NH_2$, $(CH_3O)_3$—Si—$C_3H_6$—Cl, $(CH_3O)_3$—Si—$C_3H_6$—O—C(O)—C($CH_3$)=CH, $(CH_3)_2(CH_2$=CH—$CH_2$)—Si—Cl, $(C_2H_5O)_3$—Si—$C_3H_6$—$NH_2$,

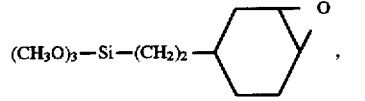

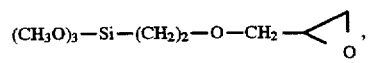

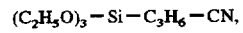

Among the various additional hydrolytically condensable silicon-containing compounds which can be used together with the silanes of formula I are the silicon-containing compounds of formula III, $$Y_nSiX_mR_{4-(n+m)} \qquad (III)$$

in an uncondensed or precondensed form,
wherein Y is a substituent including a substituted or unsubstituted 1,4,6-trioxaspiro-[4,4]-nonyl group; and n=1, 2 or 3, and
m=1, 2 or 3, with n+m necessarily≦4 and wherein R and X are as defined in formula I above.

These spirosilanes are hydrolyzable via the X group and polymerizable via the Y group and they are described in more detail in Published German Patent Application DE 41 25 201 C1.

The alkyl groups above are, e.g., straight chain, branched or cyclic groups with from 1 to 20 carbon atoms, particularly with 1 to 10 carbon atoms, and advantageously are lower alkyl groups with from 1 to 6 carbon atoms. Special examples of appropriate alkyl groups include methyl, ethyl, n-propyl, i-propyl, n-butyl, s-butyl, t-butyl, i-butyl, n-pentyl, n-hexyl, cyclohexyl, 2-ethylhexyl, dodecyl and octadecyl groups.

The alkenyl groups are, e.g., straight chain, branched or cyclic groups with from 2 to 20, advantageously from 2 to 10, carbon atoms and advantageously lower alkenyl groups with from 2 to 6 carbon atoms, such as vinyl, allyl and 2-butenyl.

Preferred aryl groups include phenyl, biphenyl and naphthyl groups.

The alkoxy, acyloxy, alkylcarbonyl, alkoxycarbonyl and amine-containing groups advantageously derived from the above-described alkyl and aryl groups. Special examples are methoxy, ethoxy, n- and i-propoxy, n- , i- , s- and t-butoxy, methylamino, ethylamino, dimethylamino, diethylamino, N-ethylanilino, acetyloxy, propionyloxy, methylcarbonyl, ethylcarbonyl, methoxycarbonyl, ethoxycarbonyl, benzyl, 2-phenylethyl and tolyl groups.

The above-named groups can have one or more substituents as needed, e.g. halogen, alkyl, hydroxyalkyl, alkoxy, aryl, aryloxy, alkylcarbonyl, alkoxycarbonyl, furfuryl, tetrahydrofurfuryl, amino, alkylamino, dialkylamino, trialkylammonium, amido, hydroxy, formyl, carboxy, mercapto, cyano, nitro, epoxy, $SO_3H$ and $PO_4H_2$.

Fluorine, chlorine and bromine are particularly preferred halogens.

Among the various additional hydrolytically condensable silicon-containing compounds which can be used together with the silanes of formula I are the silicon-containing compounds of formula IV,

in an uncondensed or precondensed form,
wherein A' is selected from the group consisting of O, S, PR''', POR''', NHC(O)O and NHC(O)NR''' groups, and R''' is selected from the group consisting of hydrogen, alkyl and aryl groups; B is a straight chain or branched organic residue and is derived from a starting compound B' having at least one C=C double bond if l=1 and if A'=NHC(O)O or NHC(O)NR''', or otherwise having at least two C=C double bond, and having from 5 to 50 carbon atoms, $R^3$ is selected from the group consisting of alkylene, arylene and alkylenearylene, n=1, 2 or 3, k=0, 1 or 2, l=0 or 1, and x=a whole number having a maximum value corresponding to the number of double bonds in the starting compound B' minus 1, but if l=1 and A is NHC(O)O or NHC(O)NR''', x=the number of double bonds in the starting compound B', and R and X are as defined in relation to the silanes of formula I.

These silanes of formula IV are described in more detail in German Published Patent Application DE 40 11 044 C2 and European Patent Application EP 04 51 709 A2.

The alkyl groups above are, e.g., straight chain, branched or cyclic groups with from 1 to 20 carbon atoms, particularly with 1 to 10 carbon atoms, and advantageously are lower alkyl groups with from 1 to 6 carbon atoms. Special examples of appropriate alkyl groups include methyl, ethyl, n-propyl, i-propyl, n-butyl, s-butyl, t-butyl, i-butyl, n-pentyl, n-hexyl, cyclohexyl, 2-ethylhexyl, dodecyl and octadecyl groups.

The alkenyl groups are, e.g., straight chain, branched or cyclic groups with from 2 to 20, advantageously from 2 to 10, carbon atoms and advantageously lower alkenyl groups with from 2 to 6 carbon atoms, such as vinyl, allyl and 2-butenyl.

Preferred aryl groups include phenyl, biphenyl and naphthyl groups.

The alkoxy, acyloxy, alkylcarbonyl, alkoxycarbonyl and amine-containing groups advantageously derived from the above-described alkyl and aryl groups. Special examples are methoxy, ethoxy, n- and i-propoxy, n- , i- , s- and t-butoxy, methylamino, ethylamino, dimethylamino, diethylamino, N-ethylanilino, acetyloxy, propionyloxy, methylcarbonyl, ethylcarbonyl, methoxycarbonyl, ethoxycarbonyl, benzyl, 2-phenylethyl and tolyl groups.

The above-named groups can have one or more substituents as needed, e.g. halogen, alkyl, hydroxyalkyl, alkoxy, aryl, aryloxy, alkylcarbonyl, alkoxycarbonyl, furfuryl, tetrahydrofurfuryl, amino, alkylamino, dialkylamino, trialkylammonium, amido, hydroxy, formyl, carboxy, mercapto, cyano, nitro, epoxy, $SO_3H$ and $PO_4H_2$.

Fluorine, chlorine and bromine are particularly preferred halogens.

The group B is derived from a substituted or unsubstituted compound B' having at least two C=C double bonds, e.g. vinyl- , allyl- , acryl- and/or methacrylate groups, and having from 5 to 50, advantageously 6 to 30 carbon atoms. Advantageously the group B is derived from asubstituted or unsubstituted compound B' having two or more acrylate and methacrylate groups.

In the event that the compound B' is substituted, the substituents can be selected from the above-described substituents.

The carbonate silanes according to the invention do not necessarily need to be isolated for further processing to obtain the poly(hetero)condensates. It is possible to make these silanes first in a dropwise process and then to hydrolytically condense them with optional additional hydrolyzable compounds.

Among the hydrolyzable aluminum-compounds useful for hydrolytic condensation with the silanes according to the invention are one or more aluminum-containing hydrolytically condensable compound of formula $AlR^o{}_3$ in an uncondensed or precondensed form, in which the $R^o$ groups are the same or different and each represent halogen, an alkoxy, an acyloxy group or hydroxy. The exact preferred definition of these various groups including the alkoxy groups can be obtained above in connection with the suitable hydrolytically condensable silicon-containing compounds. The above-named groups,can be replaced partially or entirely by chelate ligands (e.g. acetylacetone or acetoacetic ester, acetic acid).

Aluminum alkoxides and aluminum halides are suitable as the aluminum-containing hydrolytically condensable compounds. Concrete examples of these compounds include:
$Al(OCH_3)_3$, $Al(OC_2H_5)_3$, $Al(O-n-C_3H_7)_3$, $Al(O-i-C_3H_7)_3$, $Al(OC_4H_9)_3$, $Al(O-i-C_4H_9)_3$, $Al(O-s-C_4H_9)_3$, $AlCl_3$ and $AlCl(OH)_2$.

Aluminum compounds, which are liquid at room temperature, e.g. aluminum-s-butylate and aluminum-i-propylate, are especially suitable.

Among the hydrolyzable compounds useful for hydrolytic condensation with the silanes according to the invention are one or more titanium- or zirconium-containing hydrolytically condensable compound of formula $MX_yR_z$ in an uncondensed or precondensed form, wherein y=1, 2, 3 or 4, z=0, 1, 2 or 3, M is titanium or zirconium and X and R are as defined in claim 1. In preferred embodiments y=2, 3 or 4 and z=0, 1 or 2.

Ti- or Zr-complexes can be used as the titanium- or zirconium-containing hydrolytically condensable compounds. Acrylic acid and methacrylic acid are additional advantageous complex formers. Concrete examples of these useful Zr- and Ti-compounds are: $TiCl_4$, $Ti(OC_2H_5)_4$, $Ti(OC_3H_7)_4$, $Ti(O-i-C_3H_7)_4$, $Ti(OC_4H_9)_4$, $Ti(2-ethylhexoxy)_4$, $ZrCl_4$, $Zr(OC_2H_5)_4$, $Zr(OC_3H_7)_4$, $Zr(O-i-C_3H_7)_4$, $Zr(OC_4H_9)_4$, $Zr(2-ethylhexoxy)_4$ and $ZrOCl_2$.

Additional hydrolyzable compounds, which can be used to make polyheterocondensates, include, e.g., boron trihalides and boric acid esters, such as $BCl_3$, $B(OCH_3)_3$ and $B(OC_2H_5)_3$, tin tetrahalides and tin tetraalkoxides, such as, e.g., $SnCl_4$ and $Sn(OCH_3)_4$, and vanadyl compounds, such as $VOCl_3$ and $VO(OCH_3)_3$.

As already mentioned the poly(hetero)condensates can be made in the usual manner in this field. If only silicon-containing compounds are used, the hydrolytic condensation can occur chiefly because the required water is added directly to the silicon-containing compounds to be hydrolyzed, which are present as such or dissolved in a suitable solvent, at room temperature or with gentle cooling (advantageously with stirring and in the presence of hydrolysis- and condensation catalysts) and the resulting mixture is stirred for some time (one to several hours).

A stepwise addition of water is recommended when working with reactive compounds of Al, Ti or Zr. Depending on the reactivity of the particular compound the hydrolysis should be performed at temperatures between –20 and 130° C., advantageously between 0° and 30° C. and/or at the boiling point of the solvent being used. As already discussed, the optimum manner and way water is added depends above all on the reactivity of the reactant compounds used. Thus, for example, the dissolved reactant compounds can be added slowly to an excess of water dropwise or one adds water in separate portions to the dissolved reactant compounds. It can also be useful to add the water to the reaction system with the aid of a water-containing organic or inorganic system instead of as such or "as is". Moisture-bearing adsorption agents can also be used to introduce a particular amount of water to the reaction mixture, e.g. molecular sieves, and water-containing organic solvent systems, such as 80% aqueous ethanol. The water addition however can occur also via a chemical reaction, which releases water during the course of the reaction. An example of a water-producing reaction is an esterification.

The solvents which can be used include the lower aliphatic alcohols (e.g. ethanol or ketoopanol), also ketones, advantageously lower dialkyl ketones, such as acetone or methyl isobutyl ketone, ethers, advantageously lower dialkyl ethers such as diethyl ether or dibutyl ethers, THF, amides, esters, especially ethyl acetate, dimethyl formamide, tertiary amines, especially triethylamine, and their mixtures.

The hydrolysis of the carbonate-silanes advantageously is performed in basic or neutral media. Advantageously either a basic solvent, e.g. triethylamine, is used or basic hydrolysis and condensation catalysts, such as methyl imidazole, tertiary amines, etc, are added.

The reactant compounds are not necessarily all present at the beginning of hydrolysis (polycondensation), but in certain cases it is even advantageous when only a part of these compounds is first brought into contact with water and later the remainder of the compounds is added.

To avoid precipitation as much as possible during the use of various silicon-containing hydrolyzable compounds during the hydrolysis and polycondensation, the water addition can be performed in several steps, e.g. in three steps. Thus in the first step, e.g., a tenth to a twentieth of the required amount of water for hydrolysis can be added. After a brief stirring the addition of a fifth to a tenth of the required amount of water occurs and after further stirring the remainder can be added.

The condensation time adjusts itself to the reactant compounds and their amounts, the catalysts used, the reaction temperature, etc. Generally the polycondensation occurs at normal pressures, but it can also be performed at elevated or reduced pressures.

The poly(hetero)condensates thus obtained can be processed further either "as is" or after partial or complete removal of the solvent. In several cases it can be advantageous to replace the excess water and the formed and optional additional solvents by another solvent to stabilize the poly(hetero)condensate. For this purpose, the reaction mixture, e.g., can be concentrated, e.g., in vacuum at slightly elevated temperatures so that it can be received in the other solvent without difficulty.

When these poly(hetero)condensates are used as lacquers for coatings(e.g. of plastic materials such as PVC, PC, PMMA, PE, PS, etc and of glass, paper, wood, ceramics, metals, etc), thus standard lacquer additives, such as coloring agents(pigments or dyes), filling materials, oxidation inhibitors, thinning agents, UV absorbers, stabilizers or the like, can be added to them at the latest immediately prior to use. Conductivity additives (such as graphite powder or silver powder) can also be added to these compositions. In the case of molded bodies addition of inorganic and/or organic filling materials to the poly(hetero)condensate is particularly useful.

The final hardening of the poly(hetero)condensates occurs by polymerization of the polymerizable groups after addition of suitable initiators, e.g., thermal, photochemical or redox-inducing. Thus in connection with an anionic and/or covalent-nucleophilic polymerization the rings of the carbonate groups are opened and an organic network is built up. Surprisingly it was established that the volume of the poly(hetero)condensate is reduced only slightly during the course of the polymerization. With increasing numbers of carbonate groups the volume reduction is reduced so that only a slight volume reduction is obtained depending on the number of the carbonate groups. Coatings(some biologically degradable), filling materials and molded bodies as well as sealing and adhesive materials based on the silicic acid (hetero)polycondensates, which undergo a reduced hardening shrinkage on hardening, can be obtained with the aid of carbonate-silanes according to the invention.

It is also possible to add additional ionically and/or radically polymerizable components to the poly(hetero) condensates prior to polymerization and prior to the final hardening. Radically polymerizable compounds, which can be added, are, e.g., those with C=C double bonds, such as acrylate or methacrylate, in which the polymerization occurs via C=C double bonds. Ionically polymerizable compounds, which can be added, contain, e.g., ring systems, which polymerize cationically via ring opening, such as perhaps spiroorthoester, spiroorthocarbonate, bicyclic spiroorthoester, mono- or oligoepoxides. Also compounds, which are both cationically and radically polymerizable, can be added, such as methacryloyl spiroorthoester. These polymerize radically via the C=C double bond and cationically via ring opening. These systems are, e.g., described in Journal f. prakt. Chemie, Vol. 330, Part 2, 1988, pp. 316–318, or in Journal of Polymer Science: Part C: Polymer Letters, Vol. 26, pp. 517 to 520 (1988).

When the hardening of the poly(hetero)condensates occurs photochemically, photoinitiators are added; when it occurs thermally, thermal initiators are used.

Suitable initiators include, e.g., s-BuLi, $Sn(BU)_2(OCH_3)_2$, $Zn(C_2H_5)_2$, $Al(O-s-Bu)_3$, $Mg(BU)_2$, $Bu_4NF \cdot 3H_2O$ (TBAF), $[(CH_3)_2N]_3SSi(CH_3)_3F_2$ (TASF), $BF_3O(C_2H_5)_2$, $F_3CSO_3H$, $F_3CSO_3CH_3$, $SnCl_4$, $SnBr_4$, $TiCl_4$, $Bu_2SnBr_2$, $Bu_3SnOCH_3$, and the following porphyrin derivative with R=Cl, $OCH_3$, $OCH_2CH_2OC_6H_5$ or $OCH(CH_3)CH_2Cl$ wherein the porphyrin derivative has the following formula:

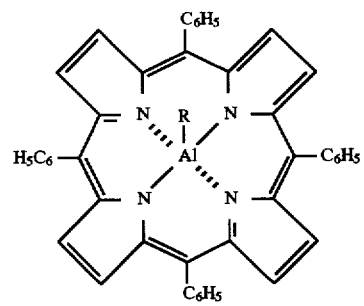

The hardening can also, e.g. in a two-component system, occur by means of diamines. The hardening is performed at room temperature or at elevated temperatures according to the reactivity of these amines.

The initiator can be added in the standard amounts. For example, the initiator can be added in an amount of, e.g. , 0.5 to 5 percent by weight, especially 1 to 3% by weight, in relation to the mixture, to a mixture which contains from 30 to 50% by weight solids (polycondensates).

If additional components, which contain reactive double bonds, such as silanes of the formula IV, besides the carbonate silanes according to the invention are used to make the poly(hetero)condensates, thus, e.g., a thermally or photochemically initiated polymerization can proceed via these double bonds.

Commercially obtained compounds can be used as photoinitiators, for example photoinitiators of the Irgacure type including Irgacure 184 (1-hydroxycyclohexylphenylketone), Irgacure 500 (1-hydroxycyclohexylphenylketone/benzophenone), and others obtainable from Ciba-Geigy; Darocure 1173, 1116, 1398, 1174 and 1020 (obtained from Merck Inc.), benzophenone, 2-chlorthioxanthon, 2-methylthioxanthon, 2-isopropylthioxanthon, benzoin, 4,4-dimethoxybenzoin, etc.

Organic peroxides in the form of diacylperoxides, peroxydicarbonates, alkylperesters, dialkylperoxides, perketals, ketoneperoxides and alkylhydroperoxides can be used as thermal initiators. Dibenzoyl peroxides, t-butylperbenzoates and azobisisobutyronitriles are preferred examples of thermal initiators.

A poly(hetero)condensate lacquer provided with an initiator based on carbonate-silanes according to the invention can then be used, e.g., for coating substrates. Standard coating methods can be used for these coatings, e.g. dipping, flooding, pouring, rolling, spraying, painting, electrostatic spraying and electroimmersion lacquering. The lacquer does not necessarily need to contain a solvent. Particularly starting material (silanes) with two alkoxy groups on a silicon atom can be processed without addition of solvents.

The applied lacquer may advantageously be dried prior to hardening. After that, it can be hardened in known ways according to the type of initiator, either thermally or photochemically. Combinations of hardening methods may of course be used.

If the hardening of the applied lacquer occurs advantageously by irradiation, after the radiative hardening a thermal hardening can be performed, particularly to remove solvent still present or to include additional reactive groups in the hardening.

Although polymerizable groups are already present in poly(hetero)condensates based on the carbonate-silanes according to the invention, it has also proven advantageous in certain cases to add additional compounds (advantageously purely organic in nature) to these condensates prior to or during further processing. Advantageously, for example, these additional compounds include acrylic acid and methacrylic acid as well as compounds derived from them, especially esters of monofunctional alcohols (e.g. $C_{1-4}$ alcohols), (meth)acrylnitrile, styrol and mixtures thereof. This type of compound can be used at the same time as a solvent and/or thinning material when the poly(hetero) condensate is used to make a lacquer coating.

Molded bodies and/or materials made from the poly(hetero)condensates based on the carbonate-silanes according to the invention can be made by any of a variety of known commercial methods which are standard in this field, e.g., by injection molding, casting, extrusion, etc. The poly(hetero)condensates based on the carbonate-silanes according to the invention are suitable also for manufacture of composite material (e.g. reinforcing glass fibers).

The carbonate-silanes according to the invention can also be used for making hydrolytically condensable polymerizates. Moreover the carbonate-silanes according to the invention, either individually or together with other radically polymerizable and/or ionically polymerizable and/or covalently-nucleophilically polymerizable components, can be polymerized, so that the final hardening then occurs by hydrolytic condensation via the hydrolytically condensable groups of the carbonate-silanes according to the invention and optional additional hydrolyzable components. In this case the organic network is built up first by polymerization and then the inorganic by hydrolytic condensation.

The polymerizate is made by ionic or covalent-nucleophilic polymerization of one or more carbonate group-containing compounds and the optionally included tonically and/or covalent-nucleophilically polymerizable compounds, and, if necessary, by radical polymerization of one or more radically polymerizable compounds, by action of heat or electromagnetic radiation and in the presence of one or more initiators and/or a solvent. The polymerizate is particularly characterized by the inclusion of 5 to 100 Mol percent, based on monomer content, of carbonate group-containing compounds selected from the silanes as defined by formula I above.

The additional ionically and/or radically and/or covalent-nucleophilically polymerizable compounds can be added to the carbonate-silanes according to the invention prior to polymerization. Radically polymerizable compounds, which can be added, are, e.g., those with C═C double bonds, such as acrylate or methacrylate, whereby the polymerization occurs via the C═C double bonds. Ionically polymerizable compounds, which can be added, include ring systems, which polymerize cationically via ring opening, such as perhaps spiroorthoester, spiroorthocarbonate, bicyclic spiroorthoester, mono- or oligoepoxides. Also compounds, which are both cationically and radically polymerizable, can be added, such as methacryloyl spiroorthoester. These polymerize radically via the C═C double bond and cationically via ring opening. These systems are, e.g., described in Journal f. prakt. Chemie, Vol. 330, Part 2, 1988, pp. 316–318, or in Journal of Polymer Science: Part C: Polymer Letters, Vol. 26, pp. 517 to 520 (1988).

Furthermore additional hydrolyzable and polymerizable compounds of silicon can be added, if necessary in condensed form, based on the carbonate-silanes according to the invention prior to polymerization, which are then copolymerized. These silicon-containing compounds which are derived, e.g., from epoxide-containing silanes, are thus cationically polymerizable and are used, among other things, for making carbonate-silanes according to the invention. These systems have already been described in detail in the sections above regarding the making of carbonate-silanes according to the invention.

Silicon-containing compounds can also be used, which are derived, e.g., from those of formula III and/or IV, and are, e.g., ionically and/or radically polymerizable. These systems are described in more detail in the sections above regarding the making of the poly(hetero)condensates.

The polymerization occurs, e.g., thermally, photochemically or is redox-induced, after addition of a suitable initiator. Thus in connection with an ionic or covalent-nucleophilic polymerization, the rings of the carbonate groups and optionally additionally polymerizable rings open, and also a radical polymerization occurs by cross-linking of double bonds. In this way the organic network is built up. Surprisingly it was established that the volume of the reaction mass is only slightly reduced during the course of the polymerization. Depending on the number of carbonate groups only a slight volume decrease is obtained because the volume decrease is reduced as the number of carbonate groups increases.

If the polymerization occurs photochemically, photoinitiators are added to the reaction mass, if it occurs thermally, thermal initiators are added. Suitable initiators have already been described in relation to the hardening of the poly(hetero)condensates If components containing double bonds are added to the carbonate-silanes according to the invention a polymerization can proceed because of this, which is initiate, e.g., thermally or photochemically.

Photoinitiators can be obtained commercially. Examples have already been described in relation to the hardening of the poly(hetero)condensates. Organic peroxides in the form of diacylperoxides, peroxydicarbonates, alkylperesters, dialkylperoxides, perketals, ketoneperoxides and alkylhydroperoxides can be used as thermal initiators. Examples have already been described in relation to the hardening of the poly(hetero)condensates.

The initiator can be added in the standard amounts. For example, the initiator can be added in an amount of, e.g., 0.5 to 5 percent by weight, especially 1 to 3% by weight, in relation to the mixture, to a mixture which contains from 30 to 50% by weight solids (polycondensates).

The polymerizate obtained in this way can be hydrolytically condensed to build up the inorganic network, in the presence of additional hydrolytically condensable compounds of silicon and of other elements from the B, Al, P, Sn, Pb periodic table group, the transition metals, the lanthanides and the actinides, as needed, and/or as precondensates derived from these additional compounds, by action of water, in the presence of a catalyst and/or a solvent as needed.

The hydrolytic condensation of the polymerizates can also be performed in acidic media in contrast to the hydrolytic condensates of the carbonate-silanes according to the invention. The polymerizates contain hydrolyzable X groups, e.g. alkoxy groups, so that an inorganic network (Si—O—Si bonds) can be built up.

Among the hydrolyzable silicon-containing compounds those of the formula II, in precondensed form, if necessary, are preferred. These systems are described already in detail in regard to the making of the poly(hetero)condensates according to the invention and are illustrated there with concrete examples.

The hydrolyzable aluminum-, titanium- and zirconium compounds used as needed are already treated in detail in regard to the making of the poly(hetero)condensates according to the invention.

Additional hydrolyzable compounds, which can be added to the polymerizates, are, e.g., borontrihalides and boric acid esters, such as $BCl_3$, $B(OCH_3)_3$ and $B(OC_2H_5)_3$, tin tetrahalides and tin tetraalkoxides, such as $SnCl_4$ and $Sn(OCH_3)_4$, and vanadyl compounds, such as, e.g., $VOCl_3$ and $VO(OCH_3)_3$.

As already mentioned the poly(hetero)condensates can be made in the usual manner in this field. The hydrolytic condensation can occur chiefly because the required water is added directly to the silicon-containing compounds to be hydrolyzed, which are present as such or dissolved in a suitable solvent, at room temperature or with gentle cooling and the resulting mixture is stirred for some time.

A stepwise addition of water is recommended when working with reactive compounds of Al, Ti or Zr. Depending on the reactivity of the particular compound the hydrolysis should be performed at temperatures between −20° and 130° C., advantageously between 0° and 30° C. and/or at the boiling point of the solvent being used. As already discussed, the optimum manner and way water is added depends above all on the reactivity of the reactant compounds used. Thus, for example, the dissolved reactant compounds can be added slowly to an excess of water dropwise or one adds water in separate portions to the dissolved reactant compounds. It can also be useful to add the water to the reaction system with the aid of a water-containing organic or inorganic system instead of as such or "as is".

The carbonate-silanes according to the invention can be modified by reaction at the carbonate groups. Thus, e.g., amines can be added to form an amide group, and a hydrolyzable and condensable amide-silane results, which can be used to make the silicic acid polycondensate and/or silicic acid(hetero)polycondensate. If diamines are added a disilane results.

It is also possible to process first the carbonate-silanes according to the invention by hydrolytic condensation to form the silicic acid polycondensates and/or silicic acid (hetero)polycondensates. These condensates can be cross-linked by addition of amines, especially diamines, i.e. for hardening. The carbonate-silanes according to the invention can thus, e.g., be used for making two-component systems.

The invention will now be illustrated in more detail with the aid of the following examples.

EXAMPLES

Example 1

Preparation of 2-oxo-1,3-dioxolan-4-methylenoxypropyltrimethoxysilane

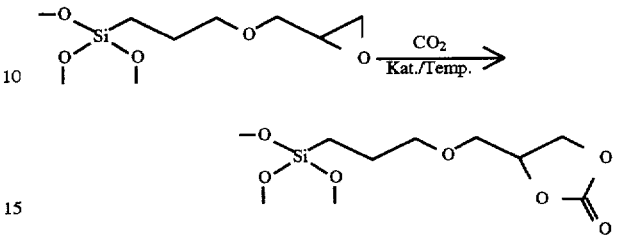

Carbon dioxide($CO_2$) is fed into a 61.2 g 3-glycidyloxypropyltrimethoxysilane (0.258 mol) after addition of a catalyst(LiI/DABCO) and the resulting mixture is heated at 100° C. The reaction is performed by an epoxide titration or gas chromatographically. After reaction is more than 95% complete, the resulting product is isolated by distillation or used directly in further processing.
Product is characterized as follows IR: $v_{C-H, allg}$=2960 to 2840 cm$^{-1}$ $v_{(OCH_3)}$=2843 cm$^{-1}$
$v_{(C=O, carbonat)}$=1798 cm$^{-1}$
Sdp.: ca. 118° C. (0.06 Torr)
GC: retention time about 14.4 min(220° C.)

If the addition is performed under pressure, i.e. in an autoclave, the reaction time is considerably shortened.

Example 2

Preparation of 2-oxo-1,3-dioxolan-4-methylenoxypropyl(methyl)dimethoxysilane

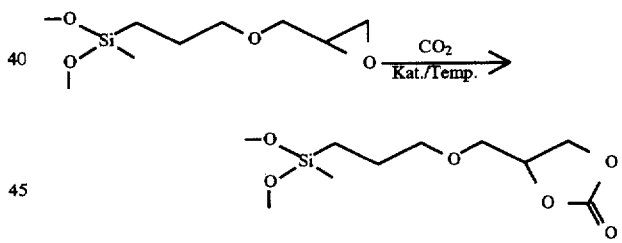

Carbon dioxide($CO_2$) is fed into a 60.0 g 3-glycidyloxypropyl(methyl)dimethoxysilane (0.242 mol) after addition of a catalyst(LiI/DABCO) and the resulting mixture is heated at 100° C. The reaction is performed by an epoxide titration or gas chromatographically. After reaction is more than 95% complete, the resulting product is isolated by distillation or used directly in further processing.
Product is characterized as follows IR: $v_{C-H, allg}$=2960 to 2840 cm$^{-1}$ $v_{(OCH_3)}$=2843 cm$^{-1}$
$v_{(C=O, carbonat)}$=1798 cm$^{-1}$
Sdp.: ca. 125° C. (0.08 Torr)
GC: retention time about 15.3 min(220° C.)

If the addition is performed under pressure, i.e. in an autoclave, the reaction time is considerably shortened.

Example 3

Production of a Disilane by Amine Addition and/or Cross-linking via the Carbonate Groups Prior to Hydrolysis and Condensation of the Silane, i.e. additional required Hydrolysis and Condensation. Isomerization is possible in regard to the OH group positions according to Ring Opening

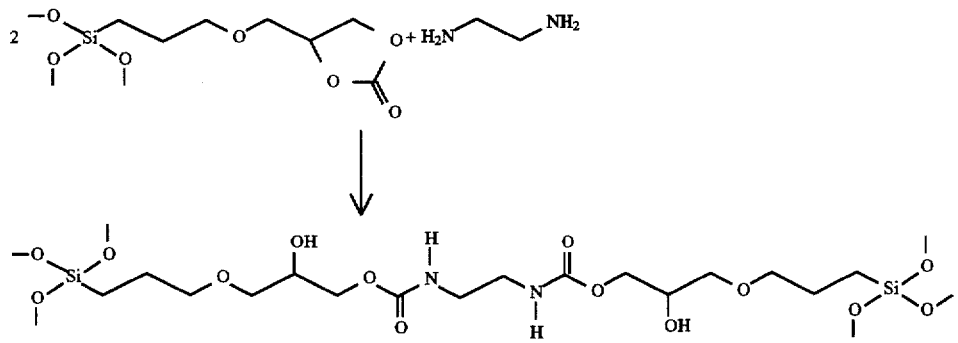

0.61g (10.7 mmol) ethylenediamine are added to 6.0 g 2-oxo-1,3-dioxlan-4-methylenoxypropyltrimethoxysilane (21.4 mmol) with stirring. The reaction is completed at room temperature after about 20 hours and is followed using IR spectroscopy.

IR: $v_{C=O, carbonate}=1798$ cm$^{-1}$ $v_{(C=O, amide)}=1720/1707$ cm$^{-1}$ $v_{(OH)}=3351$ cm$^{-1}$ The silanes can be used directly for hydrolysis and condensation and, for example, after expelling the volatile components(thermally) a nonsticky hardened coating results.

The reverse way, i.e. first hydrolysis and condensation of the Si(OR)$_3$ groups, leads to hardening by amine addition (=cross-linking). According to the reactivity of the amine groups the reaction already occurs at room temperature or at elevated temperatures. Because of that, the silanes according to the invention are usable in 2-component systems.

While the invention has been illustrated and described as embodied in hydrolyzable and polymerizable silanes, methods of making them and condensates and polymerizates made from them, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and desired to be protected by Letters Patent is set forth in the appended claims:

I claim:

1. A hydrolyzable and polymerizable silane of the formula I,

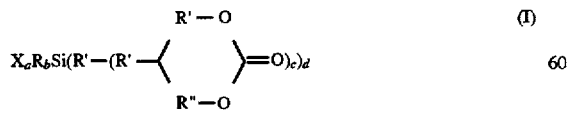

wherein X represents a member selected from the group consisting of hydrogen, halogen groups, a hydroxy group, alkoxy groups, acyloxy groups, alkylcarbonyl groups, alkoxycarbonyl groups and —NR$^2_2$ groups; and R$^2$ is a member selected from the group consisting of hydrogen, alkyl groups and aryl groups; R represents a member selected from the group consisting of alkyl groups, alkenyl groups, aryl groups, alkylaryl groups and arylalkyl groups;

wherein a=1, 2 or 3; b=0, 1 or 2; d=4–a–b; and wherein

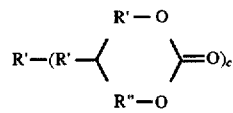

is selected from the group consisting of

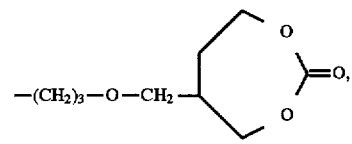

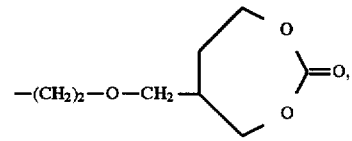

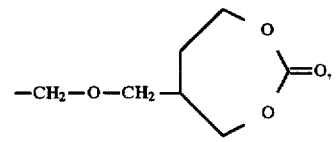

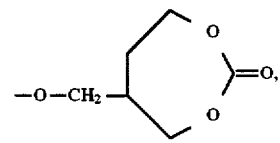

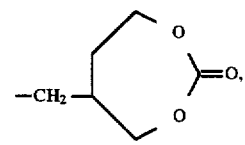

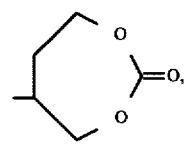

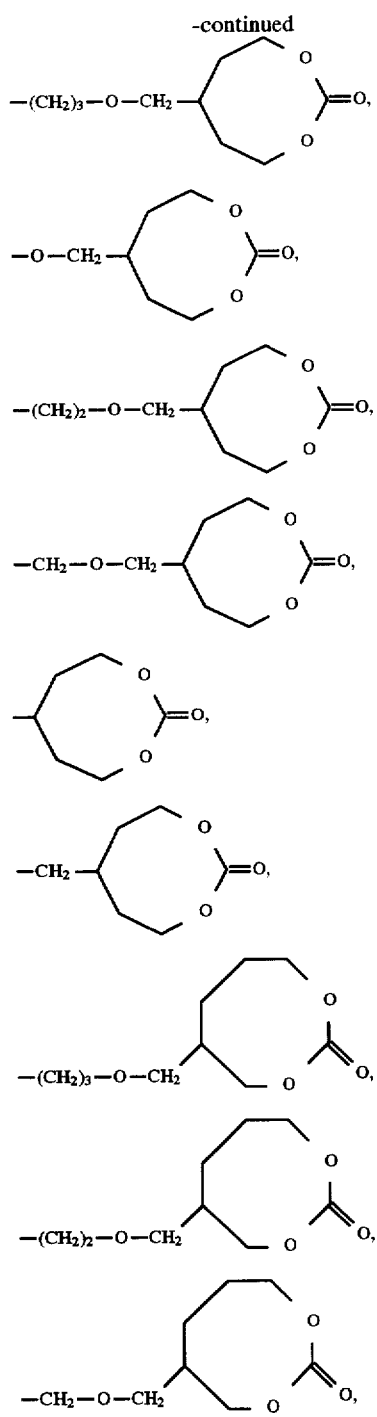
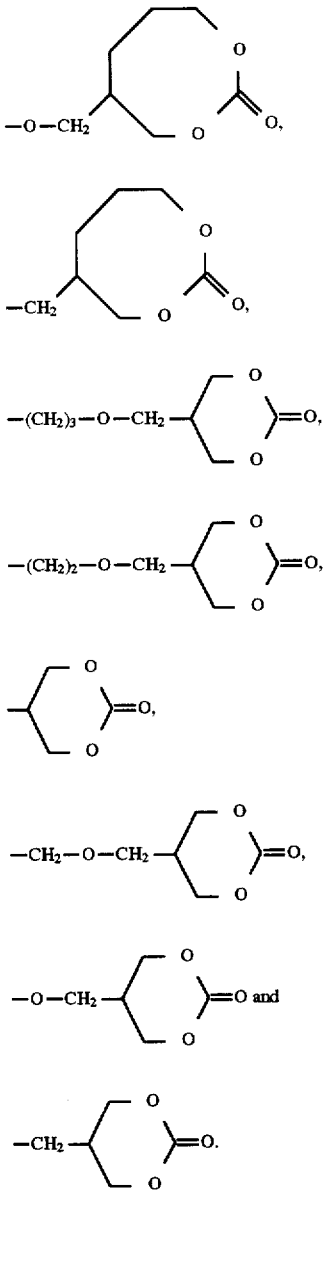
2. A hydrolyzable and polymerizable silane selected from the group consisting of:
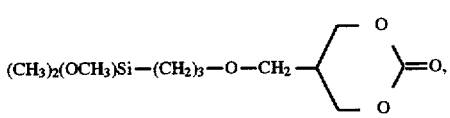
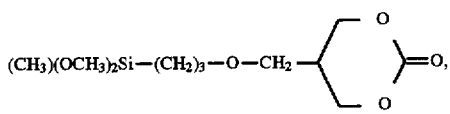

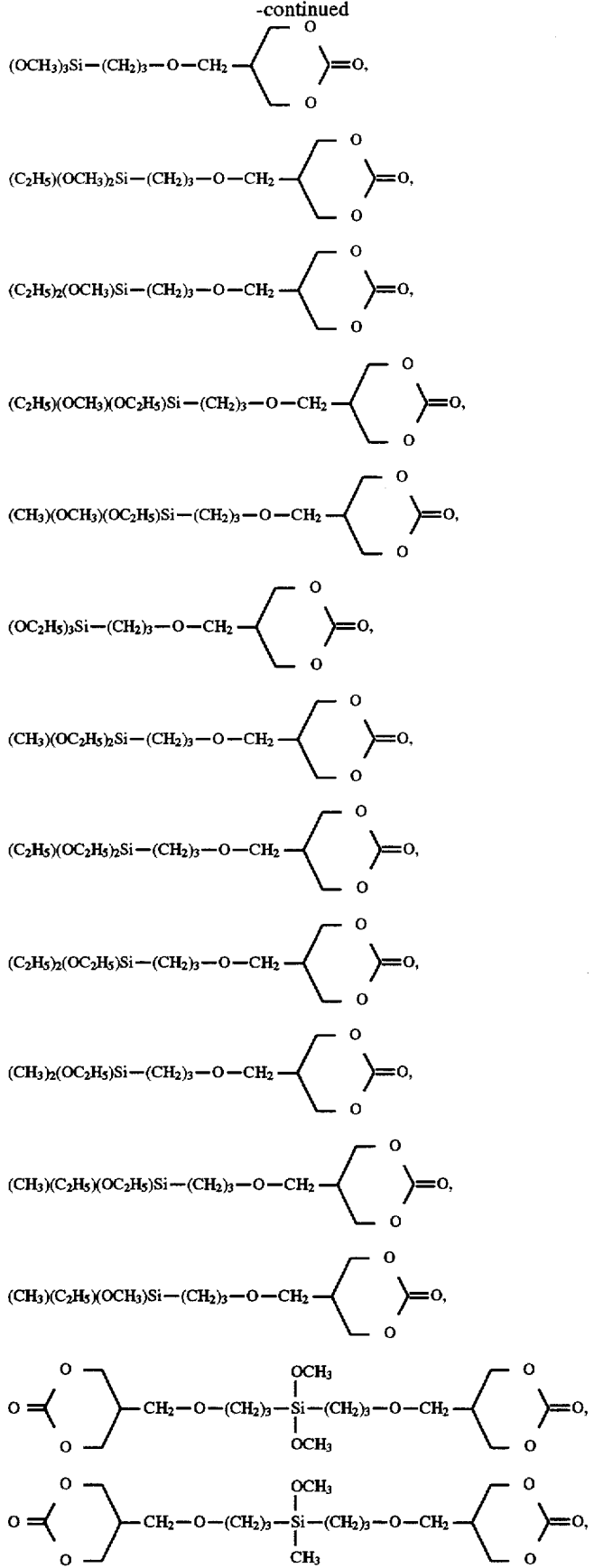

-continued
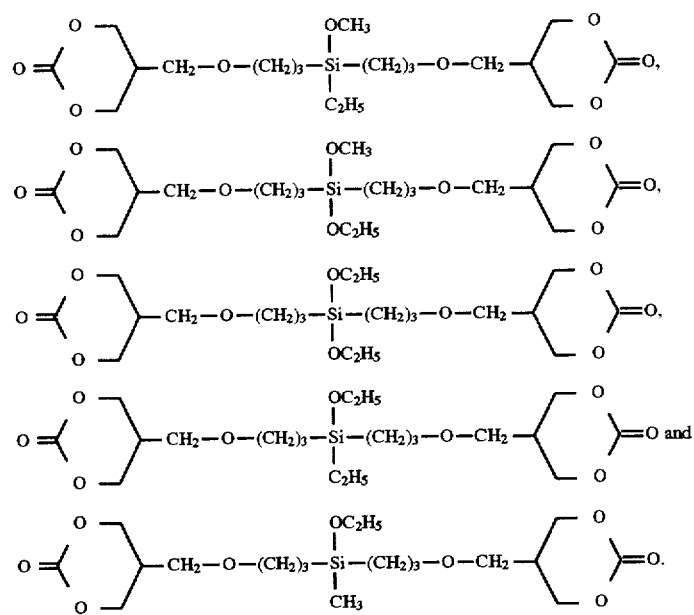
3. 2-oxo-1,3-dioxolan-4-methylenoxypropyltrimethoxysilane.
4. 2-oxo-1,3-dioxolan-4-methylenoxypropyl(methyl)dimethoxysilane.
* * * * *